(12) United States Patent
Lee et al.

(10) Patent No.: US 10,707,424 B2
(45) Date of Patent: Jul. 7, 2020

(54) SYNTHETIC METHOD OF FUSED HETEROAROMATIC COMPOUND AND FUSED HETEROAROMATIC COMPOUND AND INTERMEDIATE THEREFOR AND SYNTHETIC METHOD OF INTERMEDIATE

(71) Applicant: Samsung Electronics Co., Ltd., Suwon-si, Gyeonggi-do (KR)

(72) Inventors: Eun Kyung Lee, Seoul (KR); Eigo Miyazaki, Hwaseong-si (KR); Jeong Il Park, Seongnam-si (KR); Hyun Bum Kang, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 15/645,257

(22) Filed: Jul. 10, 2017

(65) Prior Publication Data

US 2018/0130952 A1    May 10, 2018

(30) Foreign Application Priority Data

Nov. 8, 2016 (KR) .................. 10-2016-0148340

(51) Int. Cl.
| | |
|---|---|
| *H01L 51/00* | (2006.01) |
| *H01L 51/05* | (2006.01) |
| *H01L 51/50* | (2006.01) |
| *C09K 11/06* | (2006.01) |
| *C07D 345/00* | (2006.01) |
| *C07D 517/22* | (2006.01) |

(52) U.S. Cl.
CPC ........ *H01L 51/0071* (2013.01); *C07D 345/00* (2013.01); *C07D 517/22* (2013.01); *C09K 11/06* (2013.01); *H01L 51/05* (2013.01); *H01L 51/50* (2013.01); *H01L 51/0558* (2013.01)

(58) Field of Classification Search
CPC ..... H01L 51/0071; H01L 51/50; H01L 51/05; H01L 51/0558; C09K 11/06; C07D 517/22; C07D 345/00
See application file for complete search history.

(56) References Cited

U.S. PATENT DOCUMENTS

| | | | |
|---|---|---|---|
| 7,816,673 | B2 | 10/2010 | Park et al. |
| 2002/0019370 | A1 | 2/2002 | Hegde et al. |
| 2009/0043113 | A1 | 2/2009 | Park et al. |
| 2010/0065826 | A1 | 3/2010 | Takimiya et al. |
| 2011/0166362 | A1 | 7/2011 | Miyata et al. |
| 2013/0330876 | A1 | 12/2013 | Takimiya et al. |
| 2014/0187792 | A1 | 7/2014 | Ikeda et al. |
| 2015/0239901 | A1 | 8/2015 | Takimiya et al. |
| 2016/0226005 | A1 | 8/2016 | Park et al. |
| 2017/0294593 | A1 | 10/2017 | Miyazaki et al. |

FOREIGN PATENT DOCUMENTS

| | | | |
|---|---|---|---|
| EP | 2044076 | | 4/2009 |
| EP | 2098527 A1 | | 9/2009 |
| EP | 2679592 A1 | | 1/2014 |
| EP | 2740735 A1 | * | 6/2014 .......... C07D 495/04 |
| EP | 2889300 A1 | | 7/2015 |
| EP | 3050887 A1 | | 8/2016 |
| EP | 3228622 A2 | | 10/2017 |
| JP | 2006-290192 A | | 10/2006 |
| JP | 2009-152355 A | | 7/2009 |
| JP | 2009-246140 A | | 10/2009 |
| JP | 2011-184309 A | | 9/2011 |
| JP | 2016050201 A | | 4/2016 |
| KR | 10-1314998 B1 | | 10/2013 |
| KR | 2016-0093550 A | | 8/2016 |
| WO | WO-2006/077888 A1 | | 7/2006 |
| WO | WO-2009/0009790 A1 | | 1/2009 |
| WO | WO-2011/132633 A1 | | 10/2011 |
| WO | WO-2014/024769 A1 | | 2/2014 |
| WO | WO-2015/137304 A1 | | 9/2015 |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
WickiDiff, Include vs Comprise—What's the difference, recovered from: https://wikidiff.com/include/comprise on Oct. 4, 2019, pp. 1-4. (Year: 2019).*
U.S. Appl. No. 15/392,816, filed Dec. 28, 2016.
U.S. Appl. No. 16/033,574, filed Jul. 12, 2018.
Nakano et al. "Isomerically Pure Anthra [2,3-b:6,7b']—difuran (anti-ADF), -dithiophene (anti-ADT), and -diselenophene (anti-ADS): Selective Synthesis, Electronic Structures, and Application to Organic Field-Effect Transistors," The Journal of Organic Chemistry, vol. 77, pp. 8099-8111 (2012).
Kienle, "Oxidative and Transition-Metal Catalyzed Cross-Coupling Reactions, Preparation and Coupling of S-Heterocycles," pp. 1-234 (2010).
Campeau et al., "Catalytic Direct Arylation with Aryl, Bromides, and Iodides: Intramolecular Studies Leading to New Intermolecular Reactions," J. Am. Chem. Soc. 2006, 128, pp. 581-590.
Yue et al., "Synthesis of 2,3-Disubstituted Benzo[b]thiophenes via Palladium-Catalyzed Coupling and Electrophilic Cyclization of Terminal Acetylenes," J. Org. Chem, 2002, 67, pp. 1905-1909.
Partial European Search Report dated Jun. 13, 2017, for corresponding European Patent Application No. 17162097.4.

(Continued)

*Primary Examiner* — Paul A Zucker
(74) *Attorney, Agent, or Firm* — Harness, Dickey & Pierce, P.L.C.

(57) ABSTRACT

A method of making a chemical product includes reacting a compound represented by Chemical Formula 1 with a metal alkyl chalcogenide using a palladium catalyst and a tertiary phosphine catalyst to obtain a first intermediate represented by Chemical Formula 2, obtaining a second intermediate represented by Chemical Formula 3 from the first intermediate, obtaining a third intermediate from the second intermediate and a compound represented by Chemical Formula 4, obtaining a fourth intermediate including a chalcogen-containing ring from the third intermediate, and performing a cyclization reaction of the fourth intermediate to obtain a fused heteroaromatic compound. A fused heteroaromatic compound obtained by the method, an intermediate thereof, and a synthetic method of the intermediate are disclosed.

30 Claims, 1 Drawing Sheet

(56) References Cited

OTHER PUBLICATIONS

Truong, Minh Anh et al., "Synthesis of Benzofuro- and Indolo[3,2-b]indoles via Palladium-Catalyzed Double N -Arylation and Their Physical Properties", The Journal of Organic Chemistry, vol. 80, No. 22, Nov. 20, 2015, pp. 11566-11572, XP055374329, ISSN: 0022-3263, DOI: 10.1021/acs.joc.5b0286.
Takahashi, Motonobu et al, "Synthesis and Properties of Benzophospholo[3,2- b]benzofuran Derivatives", The Journal of Organic Chemistry, vol. 80, No. 8, Apr. 17, 2015, pp. 3790-3797, XP055374562, ISSN: 0022-3263, DOI: 10.1021/jo502889r.
Mehta, et al. "Iodine/Palladium Approaches to the Synthesis of Polyheterocyclic Compounds," J. Org. Chem., American Chemical Society, vol. 75, pp. 1652-1658 (2010).
Gopi, et al. "Synthesis of Fused Bromofurans via Mg-Mediated Dibromocyclopropanation of Cycloalkanone-Derived Chalcones and Cloke-Wilson Rearrangement," The Journal of Organic Chemistry, American Chemical Society, vol. 78, pp. 910-919 (2012).
Boyer, et al. "Domino rhodium(I)-catalysed reactions for the efficient synthesis of substituted benzofurans and indoles," Tetrahedron, Elsevier Science Publishers, vol. 66, pp. 6468-6482 (2010).
Saito, et al. "Facile synthesis of [1]benzothieno[3,2-b]benzothiophene from o-dihalostilbenes," Tetrahedron Letters, vol. 51, pp. 5277-5280 (2010).
Gwiazda, et al. "Highly Substitute Imidazole Derivatives from a New-Four Component Synthesis Employing Methoxyallene," Practical Synthetic Procedures, No. 6, pp. 0990-0994 (2008).
Harrowven, et al. "The synthesis of a Combrelaslatin A-4 Based Library and Discovery of New Cooperative ortho-Effects in Wittig Reactions Leading to (Z)-Stilbenes," Synlett Letter, No. 18, pp. 2977-2980 (2006).
Biniek "New Fused Bis-Thienobenzothienothiophene Copolymers and Their Use in Organic Solar Cells and Transistors," Macromolecules, American Chemical Society, vol. 46, pp. 727-735 (2013).
Kikumoto, et al. "Substituted (w-Aminoalkoxy)stilbene Derivatives as a New Class of Anticovulsants," J. Med. Chem., American Chemical Society, vol. 27, pp. 645-649 (1984).
Wan, et al. "Novel Ladder π-Conjugated Materials-Sila-Pentathienoacenes: Synthesis, Structure, and Electronic Properties," Chem. Asian. J., vol. 5, pp. 2290-2296 (2010).
Extended European Search Report dated Oct. 12, 2017, issued in corresponding European Application No. 17162097.4.
Tseng et al., "Synthesis and biological evaluation of novel symmetry bis-enediynes", European Journal of Medicinal Chemistry, 44 (2009) 35-41.
Dong, H. "25th Anniversary Article: Key Points for High-Mobility Organic Field-Effect Transistors," Advanced Materials, vol. 25, No. 43, pp. 6158-6183 (2013).
Konstantin Grenader et al.; Catalytic C—Se Bond Formation under Vey Mild Conditions for the Two-Step, One-Pot Synthesis of Aryl Selenoacetates; Adv. Synth. Catal.; 2012, pp. 2653-2658.
Hong Ahn et al.; :A Facile One-Pot Preperation of Organoselanyltrifluoroborates from Dihalobenzenes and Their Cross-Coupling Reaction; ,American Chemical Society; 2009 Organic Letters; Vo. 11, No. 2; pp. 361-364.
I.P. Beletskaya et al., "Tributyltin Aryl Selenides as Efficient Arylselenating Agents. Synthesis of Diaryl and Aryl Organyl Selenides" Russina Journal of Organic Chemestry, Vo. 37, No. 10, 2001, pp. 1463-1475.
Alain Krief et al.; "Reactions of Organic Selenocyanates with Hydroxides; The One-Pot Synthesis of Dialkyl Diselenides from Alkyl Bromides"; Agnew Chem. Int. Ed.; 2000; vol. 39; No. 9; pp. 1669-1672.
Marcelle Tiecco et al.; "Nucleohilic Aromatic Substitutions of Unactivated Aryl Halides by Methyl Selenide Anions. Synthesis and Selective Dealkylations of Aryl Alkyl Selenides." ;American Chemical Society; 1983 J. Org. Chem.; vol. 48; pp. 4289-4296.
Lars Engman et al.; "A General Procedure for the Synthesis of Methylthio-Methylseleno- and Methyltelluro-Sunstituted Aromatic Compounds"; Jouran of Organometellic Chemestry; 1985; 296; pp. 357-366.
Marialuisa Aufiero et. al.; "Highly Efficient C—SeCF3 Coupling of Aryl Iodides Enabled by an Air-Stable Dinuclear Pd Catalyst."; Agnew Chem Int. Ed.; 2015; 54; pp. 10322-10326.
Nakano, et al. "Isomerically Pure Anthra [2,3-b:6,7-b']-difuran (anti-ADF), -dithiophene (anti-ADT), and -diselenophene (anti-ADS): Selective Synthesis, Electronic Structures, and Application to Organic Field-Effect Transistors," The Journal of Organic Chemistry, vol. 77, No. 18, pp. 8099-8111 (2012).
Evers, et al. "New Synthetic Methods : Sodium Alkanechalcogenates As Demethylating Agents, Scope, Limitation and New One-Pot Synthesis of Diaryldiselenides," Tetrahedron Letters, vol. 24, No. 4, pp. 377-380 (1983).
Poon, et al. "In Search of Catalyic Antioxidants-(alkyltelluro)phenols, (Alkyltelluro)resorcinols, and Bis(alkyltelluro)phenols," The Journal of Organic Chemistry, vol. 78, pp. 6008-6015 (2013).
Grimaldi, et al. "(Biphenyl-2-alkyne) derivatives as common precursors for the synthesis of 9-iodo-10-organochalcogen-phenanthrenes and 9-organochalcogen-phenanthrenes," Organic & Biomolecular Chemistry, vol. 14, No. 44, pp. 10415-10426 (2016).
Luxen Andre, et al. "Synthese nouvelle et 15 rapide d'alkylseleno et alkyltelluroarenes au moyen d'ethers-couronnes," Tetrahedron Letters, vol. 23, No. 38, pp. 3905-3908 (1982).
Mantovani, Anderson C., et al. "Chalcogenoalkynes: Precursors for the Regioselective Preparation of 2-Chalcogeno-1-halonaphthalenes through [4+2] Cycloaddition," European Journal of Organic Chemistry, pp. 4574-4579 (Retrieved from the CA Database online) (2012).
Gazizov, I.G. et al. "Thio- and selenoanisoles in complexation reactions with iodine," Chemical Abstracts Service, pp. 1-2 (Retrieved from the CA Database online) (1984).
Iwaoka, et al. "Physical-and Bio-Organic Chemistry on Nonbonded Selenium.cntdot..cntdot..cntdot.Oxygen Interactions," Chemical Abstracts Services, pp. 1 (Retrieved from the CA Database online) (2005).
Furin, et al. "15N, 17O, 31P and 77Se Nuclear Magnetic Resonance Spectra of Polyfluoroaromatic Compounds," Journal of Fluorine Chemistry, vol. 22, No. 3, pp. 231-252 (1983).
Evers, et al. "Aryl Arylazo sulfones chemistry. 2. Reactivity toward alkaline alkane-and arene selenolate and alkane- and arenetellurolate anions," Jounral of Organic Chemistry, vol. 51, pp. 5196-5198 (1986).
European Search Report dated Apr. 5, 2018 issued in European Application No. 17199632.5.
Office Action for U.S. Appl. No. 16/033,574 dated May 7, 2019.
Zhang, B., "Palladium-catalyzed highly regioselective 2-alkynylation of 2, x-dihalopyridines." Tetrahedron 72.22 (2016): 2813-2817.
Calandra, N.A., "Development of enantioselective synthetic routes to the hasubanan and aculumine alkaloids." The Journal of organic chemistry 78.20 (2013): 10031-10057.
Mizuta, S., "Redox chemistry of trifluoromethyl sulfonium salts as CF3 radical sources." Journal of Floruine Chemistry 155 (2013): 124-131.
Kadoya, N., "Palladium (II)-catalyzed asymmetric cycloisomerization of enynes for axially chiral biaryl construction" Tetrahedron Letters 54.6 (2013): 512-514.
Kadoya, N., "Palladium (II)-catalyzed asymmetric cycloisomerization of enynes for axially chiral biaryl construction" Tetrahedron Letters 54.6 (2013): 512-514; Supplemental Information p. 1-25.
Cho, C-H. "Parallel synthesis of a desketoraloxifene analogue library via iodocyclization/palladium-catalyzed coupling." ACS combinatorial science 13.5 (2011): 501-510.
Moslin, R.M., "Synthesis of conjugated polymers containing cis-phenylenevinylenes by titanium-mediated reductions." Macromolecules 42.1 (2009): 452-454.
Moslin, R.M., "Synthesis of conjugated polymers containing cis-phenylenevinylenes by titanium-mediated reductions." Macromolecules 42.1 (2009): 452-454; Supplemental Information p. S1-S13.

(56) References Cited

OTHER PUBLICATIONS

G. Dai et al., 'Z-Shaped Pentaleno-Acene Dimers with High Stability and Small Band Gap' *Angewandte Chemie, Intl. Ed.*, vol. 55, No. 8, Feb. 2016, pp. 2693-2696.

T. Hamura et al., 'Catalytic Generation of Arynes and Trapping by Nucleophilic Addition and Iodination' *Angewandte Chemie Intl. Ed.*, vol. 51, No. 14, Apr. 2012, pp. 3368-3372.

O. R'kyek et al., 'A General Palladium-Catalyzed Sonogashira Coupling of Aryl and Heteroaryl Tosylates' *Chemistry—A European Journal*, vol. 16, No. 33, Sep. 2010, pp. 9986-9989.

Office Action dated Dec. 13, 2019, issued in corresponding European Patent Application No. 17162097.4.

* cited by examiner

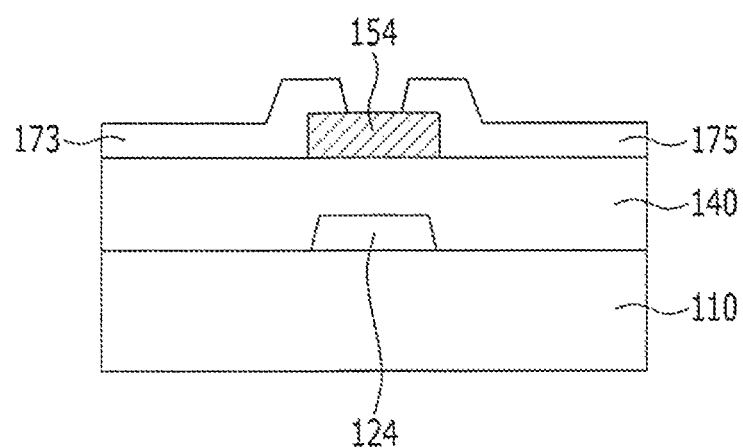

SYNTHETIC METHOD OF FUSED HETEROAROMATIC COMPOUND AND FUSED HETEROAROMATIC COMPOUND AND INTERMEDIATE THEREFOR AND SYNTHETIC METHOD OF INTERMEDIATE

CROSS-REFERENCE TO RELATED APPLICATION

This application claims priority to and the benefit of Korean Patent Application No. 10-2016-0148340 filed in the Korean Intellectual Property Office on Nov. 8, 2016, the entire contents of which are incorporated herein by reference.

BACKGROUND

1. Field

Example embodiments provide a synthetic method of a fused heteroaromatic compound, a fused heteroaromatic compound, and an intermediate therefor, and a synthetic method of the intermediate.

2. Description of Related Art

A flat panel display, such as a liquid crystal display (LCD) or an organic light emitting diode (OLED) display, includes a thin film transistor (TFT) that is a three-terminal element as a switch. Research on an organic thin film transistor (OTFT) including an organic semiconductor, such as a low molecular semiconductor or polymer semiconductor instead of an inorganic semiconductor (e.g., a silicon (Si) semiconductor as one kind of the thin film transistor), are being actively conducted. The organic thin film transistor may be made into a fiber or a film due to characteristics of an organic material, and thus is drawing attention as an element for a flexible display device. The organic thin film transistor may be manufactured using a solution process such as inkjet printing, and may be easily applied to a large area flat panel display where a deposition process has a limit.

SUMMARY

Some example embodiments provide a synthetic method of a fused heteroaromatic compound that is applicable as an organic semiconductor.

Some example embodiments provide a fused heteroaromatic compound obtained by the synthetic method.

Some example embodiments provide a novel intermediate of the fused heteroaromatic compound.

Some example embodiments provide a synthetic method of the intermediate.

Some example embodiments provide an electronic device including the fused heteroaromatic compound.

According to some example embodiments, a method of making a chemical product includes reacting a compound represented by Chemical Formula 1 with a metal alkyl chalcogenide using a palladium catalyst and a tertiary phosphine catalyst to obtain a first intermediate represented by Chemical Formula 2, obtaining a second intermediate represented by Chemical Formula 3 from the first intermediate, obtaining a third intermediate from the second intermediate and a compound represented by Chemical Formula 4, obtaining a fourth intermediate including a chalcogen-containing ring from the third intermediate, and performing a cyclization reaction of the fourth intermediate to obtain a fused heteroaromatic compound.

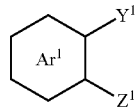

[Chemical Formula 1]

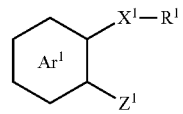

[Chemical Formula 2]

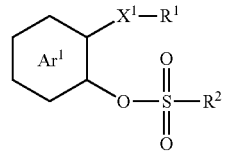

[Chemical Formula 3]

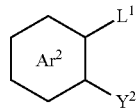

[Chemical Formula 4]

In Chemical Formulae 1 to 4, $Ar^1$ and $Ar^2$ are independently one of a substituted or unsubstituted aromatic ring, a substituted or unsubstituted heteroaromatic ring, and a combination thereof in a fused ring, $Y^1$ and $Y^2$ are independently one of a halogen element or a C1 to C10 haloalkyl group, $Z^1$ is one of a C1 to C10 alkoxy group, a C1 to C10 haloalkyl group, or a halogen element, provided that $Z^1$ is different from $Y^1$, $X^1$ is one of Se or Te, $R^1$ is one of a substituted or unsubstituted C1 to C10 alkyl group, $R^2$ is one of hydrogen, a substituted or unsubstituted C1 to C20 alkyl group, a C1 to C20 haloalkyl group, a substituted or unsubstituted C6 to C20 aryl group, halogen element, or a combination thereof, and $L^1$ is one of an ethenyl group or an ethynyl group.

In some example embodiments, the tertiary phosphine catalyst may include a metal-free tertiary phosphine catalyst.

In some example embodiments, the metal free tertiary phosphine catalyst may be represented by Chemical Formula 5.

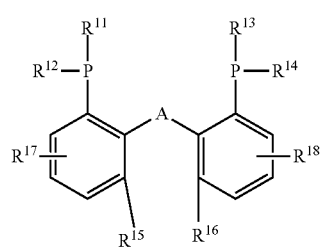

[Chemical Formula 5]

In Chemical Formula 5,

A is one of a single bond, a substituted or unsubstituted C1 to C3 alkylene group, or oxygen (O), $R^{11}$ to $R^{14}$ are one of independently a substituted or unsubstituted C6 to C12 aryl group or a substituted or unsubstituted C3 to C12 cycloalkyl group, $R^{15}$ to $R^{18}$ are one of independently hydrogen, a substituted or unsubstituted C1 to C10 alkyl group, a substituted or unsubstituted C6 to C20 aryl group, or a substituted or unsubstituted C3 to C20 cycloalkyl group, and $R^{15}$ and $R^{16}$ are independently present or are linked to provide a ring.

In some example embodiments, the metal free tertiary phosphine catalyst may include one of bis[2-(diphenylphosphino)phenyl]methane, bis[2-(diphenylphosphino)phenyl]ether, bis[2-(di-o-tolyphosphino)phenyl]ether, bis[2-(dicyclohexylphosphino)phenyl]ether, 4,6-bis(diphenylphosphino)dibenzofuran, or a combination thereof.

In some example embodiments, the palladium catalyst may include tris(dibenzylideneacetone)dipalladium(0).

In some example embodiments, the reacting the compound represented by Chemical Formula 1 with the metal alkyl chalcogenide may include obtaining the metal alkylyl chalcogenide from an alkyl chalcogenide derivative and a metal salt.

In some example embodiments, the metal salt may include at least one of an alkali metal, an alkaline-earth metal, and a transition metal.

In some example embodiments, the metal salt may include at least one of $NaBH_4$ and $LiAlH_4$.

In some example embodiments, the reacting the compound represented by Chemical Formula 1 with the metal alkyl chalcogenide may be include obtaining the metal alklyl chalcogenide from metal salt and a chalcogen element (e.g., Se and Te).

In some example embodiments, the metal salt may include at least one of an alkali metal, an alkaline-earth metal, and a transition metal.

In some example embodiments, the metal salt may include at least one of methyl lithium ($LiCH_3$) and methyl magnesium bromide ($CH_3MgBr$).

In some example embodiments, the obtaining the third intermediate may include supplying a halogen salt to the second intermediate.

In some example embodiments, the obtaining the third intermediate may include supplying to the second intermediate one of potassium iodide, copper iodide, or a combination thereof.

In some example embodiments, the obtaining the fourth intermediate may include supplying a halogen molecule to the third intermediate.

In some example embodiments, the performing the cyclization reaction may include supplying a chalcogen element to the third intermediate.

In some example embodiments, the third intermediate may be represented by Chemical Formula 6.

[Chemical Formula 6]

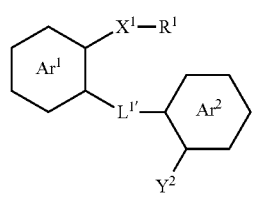

In Chemical Formula 6, $Ar^1$ and $Ar^2$ are independently one of a substituted or unsubstituted aromatic ring, a substituted or unsubstituted heteroaromatic ring, and a combination thereof in a fused ring, $X^1$ is one of Se or Te, $R^1$ is one of a substituted or unsubstituted C1 to C10 alkyl group, $L^{1\prime}$ is one of an ethenylene group or an ethynylene group, and $Y^2$ is one of a halogen element or a C1 to C10 haloalkyl group.

In some example embodiments, the fourth intermediate may be represented by Chemical Formula 7.

[Chemical Formula 7]

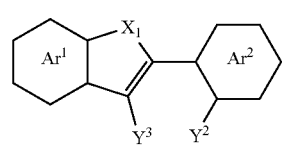

In Chemical Formula 7, $Ar^1$ and $Ar^2$ are independently one of a substituted or unsubstituted aromatic ring, a substituted or unsubstituted heteroaromatic ring, and a fused ring of the foregoing two or more rings, $X^1$ is one of Se or Te, and $Y^2$ and $Y^3$ are independently one of a halogen element or a C1 to C10 haloalkyl group.

In some example embodiments, the fused heteroaromatic compound may be represented by Chemical Formula 8.

[Chemical Formula 8]

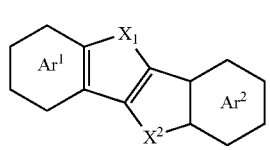

In Chemical Formula 8, $Ar^1$ and $Ar^2$ are independently one of a substituted or unsubstituted aromatic ring, a substituted or unsubstituted heteroaromatic ring, and a fused ring of the foregoing two or more rings, $X^1$ is one of Se or Te, and $X^2$ is one of O, S, Se, or Te.

The $Ar^1$ and $Ar^2$ are independently one of a benzene, a naphthalene, an anthracene, a tetracene, a pentacene, a thiophene, a selenophene, a tellurophene, a furane, a pyrrole, and a fused ring of the foregoing two or more rings.

According to some example embodiments, an intermediate represented by Chemical Formula 2 is provided.

[Chemical Formula 2]

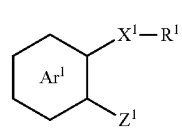

In Chemical Formula 2,

Ar$^1$ is one of a substituted or unsubstituted aromatic ring, a substituted or unsubstituted heteroaromatic ring, and a combination thereof in a fused ring, X$^1$ is one of Se or Te, R$^1$ is one of a substituted or unsubstituted C1 to C10 alkyl group, and Z$^1$ is one of a C1 to C10 alkoxy group, a C1 to C10 haloalkyl group, or a halogen element.

In some example embodiments, the Ar$^1$ may be one of a benzene, a naphthalene, an anthracene, a tetracene, a pentacene, a thiophene, a selenophene, a tellurophene, a furane, a pyrrole, and a combination thereof in a fused ring.

According to some example embodiments, a method of making a chemical product includes reacting a compound represented by Chemical Formula 1 with a metal alkyl chalcogenide using a palladium catalyst and a tertiary phosphine catalyst to obtain an intermediate represented by Chemical Formula 2.

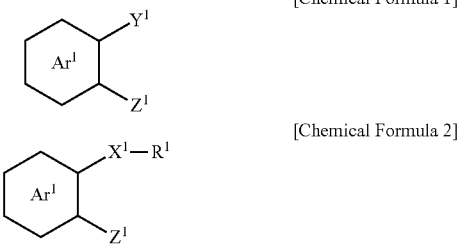

[Chemical Formula 1]

[Chemical Formula 2]

In Chemical Formulae 1 and 2,

Ar$^1$ is one of a substituted or unsubstituted aromatic ring, a substituted or unsubstituted heteroaromatic ring, and a combination thereof in a fused ring, Y$^1$ is one of a halogen element or a C1 to C10 haloalkyl group, Z$^1$ is one of a C1 to C10 alkoxy group, a C1 to C10 haloalkyl group, or a halogen element, provided that Z$^1$ is different from Y$^1$, X$^1$ is one of Se or Te, and R$^1$ is one of a substituted or unsubstituted C1 to C10 alkyl group.

In some example embodiments, the tertiary phosphine catalyst may include a metal-free tertiary phosphine catalyst.

In some example embodiments, the metal free tertiary phosphine catalyst may be represented by Chemical Formula 5.

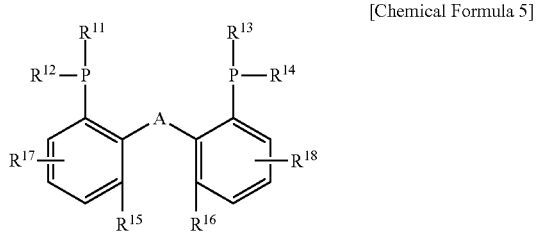

[Chemical Formula 5]

In Chemical Formula 5,

A is one of a single bond, a substituted or unsubstituted C1 to C3 alkylene group, or oxygen (O), R$^{11}$ to R$^{14}$ are one of independently a substituted or unsubstituted C6 to C12 aryl group or a substituted or unsubstituted C3 to C12 cycloalkyl group, R$^{15}$ to R$^{18}$ are one of independently hydrogen, a substituted or unsubstituted C1 to C10 alkyl group, a substituted or unsubstituted C6 to C20 aryl group, or a substituted or unsubstituted C3 to C20 cycloalkyl group, and R$^{15}$ and R$^{16}$ are independently present or are linked to provide a ring.

In some example embodiments, the metal-free tertiary phosphine catalyst may include one of bis[2-(diphenylphosphino)phenyl]methane, bis[2-(diphenylphosphino)phenyl]ether, bis[2-(di-o-tolylphosphino)phenyl]ether, bis[2-(dicyclohexylphosphino)phenyl]ether, 4,6-bis(diphenylphosphino)dibenzofuran, or a combination thereof.

In some example embodiments, the palladium catalyst may include tris(dibenzylideneacetone)dipalladium(0).

In some example embodiments, the reacting the compound represented by Chemical Formula 1 with the metal alkyl chalcogenide may include obtaining the metal alklyl chalcogenide from an alkyl chalcogenide derivative and a metal salt.

In some example embodiments, the metal salt may include at least one of an alkali metal, an alkaline-earth metal, and a transition metal.

In some example embodiments, the metal salt may include at least one of NaBH$_4$ and LiAlH$_4$.

In some example embodiments, the reacting the compound represented by Chemical Formula 1 with the metal alkyl chalcogenide may be include obtaining the metal alkyl chalcogenide from metal salt and a chalcogen element (e.g., Se and Te).

In some example embodiments, the metal salt may include at least one of an alkali metal, an alkaline-earth metal, and a transition metal.

In some example embodiments, the metal salt may include at least one of methyl lithium (LiCH$_3$) and methyl magnesium bromide (CH$_3$MgBr).

According to some example embodiments, a chemical product obtained by the method is provided.

According to some example embodiments, an electronic device including the chemical product is provided.

According to some example embodiments, a method of making a chemical product includes forming a first intermediate compound from a reaction between a compound represented by Chemical Formula 1 and a metal alkyl chalcogenide using a metal catalyst and a phosphine catalyst, the first intermediate compound being represented by Chemical Formula 2.

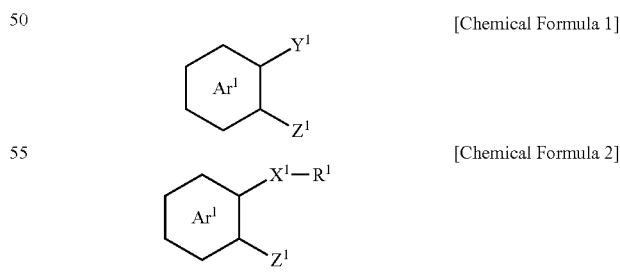

[Chemical Formula 1]

[Chemical Formula 2]

In Chemical Formulae 1 and 2,

Ar$^1$ is one of a substituted or unsubstituted aromatic ring, a substituted or unsubstituted heteroaromatic ring, and a combination thereof in a fused ring, Y$^1$ is one of a halogen element or a C1 to C10 haloalkyl group, $Z^1$ is one of a C1 to C10 alkoxy group, a C1 to C10 haloalkyl group, or a halogen element, provided that $Z^1$ is different from $Y^1$, $X^1$ is one of Se or Te, and $R^1$ is one of a substituted or unsubstituted C1 to C10 alkyl group.

In some example embodiments, the method may further include obtaining a second intermediate represented by Chemical Formula 3 from the first intermediate compound, and obtaining a third intermediate compound represented by Chemical Formula 6 from the second intermediate compound and a compound represented by Chemical Formula 4

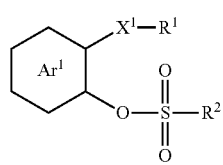

[Chemical Formula 3]

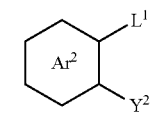

[Chemical Formula 4]

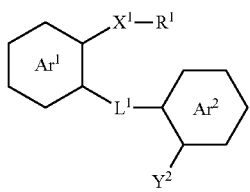

[Chemical Formula 6]

In Chemical Formulae 3 to 4 and 6, $Ar^1$ and $Ar^2$ are independently one of a substituted or unsubstituted aromatic ring, a substituted or unsubstituted heteroaromatic ring, and a combination thereof in a fused ring, $Y^1$ and $Y^2$ are independently one of a halogen element or a C1 to C10 haloalkyl group, $X^1$ is one of Se or Te, $R^1$ is one of a substituted or unsubstituted C1 to C10 alkyl group, $R^2$ is one of hydrogen, a substituted or unsubstituted C1 to C20 alkyl group, a C1 to C20 haloalkyl group, a substituted or unsubstituted C6 to C20 aryl group, halogen element, or a combination thereof, $L'$ is one of an ethenyl group or an ethynyl group, and $L^{1\prime}$ is one of an ethenylene group or an ethynylene group.

In some example embodiments, the method may further include obtaining a fourth intermediate compound including a chalcogen-containing ring from the third intermediate compound, wherein the fourth intermediate compound is represented by Chemical Formula 7:

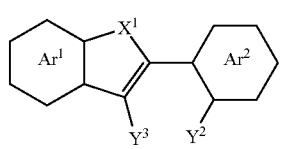

[Chemical Formula 7]

In Chemical Formula 7, $Ar^1$ and $Ar^2$ are independently one of a substituted or unsubstituted aromatic ring, a substituted or unsubstituted heteroaromatic ring, and a fused ring of the foregoing two or more rings, $X^1$ is one of Se or Te, and $Y^2$ and $Y^3$ are independently one of a halogen element or a C1 to C10 haloalkyl group.

In some example embodiments, the method may further include performing a cyclization reaction of the fourth intermediate compound to obtain a fused heteroaromatic compound represented by Chemical Formula 8:

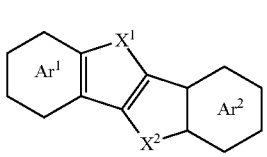

[Chemical Formula 8]

In Chemical Formula 8, $Ar^1$ and $Ar^2$ are independently one of a substituted or unsubstituted aromatic ring, a substituted or unsubstituted heteroaromatic ring, and a fused ring of the foregoing two or more rings, $X^1$ is one of Se or Te, and $X^2$ is one of O, S, Se, or Te.

In some example embodiments, $Ar^1$ and $Ar^2$ are independently one of a benzene, a naphthalene, an anthracene, a tetracene, a pentacene, a thiophene, a selenophene, a tellurophene, a furane, a pyrrole, and a fused ring of the foregoing two or more rings.

BRIEF DESCRIPTION OF THE DRAWING

A cross-sectional view showing an organic thin film transistor according to some example embodiments is shown.

DETAILED DESCRIPTION

Hereinafter, some example embodiments will hereinafter be described in detail, and may be easily performed by those who have common knowledge in the related art. However, inventive concepts may be embodied in many different forms and is not to be construed as limited to the example embodiments set forth herein.

As used herein, when a definition is not otherwise provided, the term 'substituted' refers to replacement by a substituent selected from a halogen atom, a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof, instead of hydrogen of a compound.

As used herein, when a definition is not otherwise provided, the term 'hetero' refers to one including 1 to 4 heteroatoms selected from N, O, S, Se, Te, Si, and P.

Hereinafter, a synthetic method of a fused heteroaromatic compound according to some example embodiments is described.

According to the synthetic method of a fused heteroaromatic compound of some example embodiments, a novel intermediate such as an alkyl seleno derivative or an alkyl telluro derivative is obtained from a novel reactant, and then, a fused heteroaromatic compound having selenium (Se) or tellurium (Te) may be easily obtained from the novel intermediate.

The synthetic method of a fused heteroaromatic compound according to some example embodiments includes reacting a cyclic compound substituted with a halogen or a halogen-containing group with a metal alkyl chalcogenide to obtain a first intermediate, substituting the first intermediate to obtain a second intermediate, substituting the second intermediate to obtain a third intermediate having a structure where two rings are linked each other, obtaining a fourth intermediate including a chalcogen-containing ring from the third intermediate, and obtaining a fused heteroaromatic compound by a cyclization reaction of the fourth intermediate.

The first intermediate may be obtained by reacting a compound represented by Chemical Formula 1 with a metal alkyl chalcogenide.

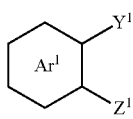

[Chemical Formula 1]

In Chemical Formula 1, $Ar^1$ is one of a substituted or unsubstituted aromatic ring, a substituted or unsubstituted heteroaromatic ring, and a fused ring of the foregoing two or more rings, $Y^1$ is a halogen element or a C1 to C10 haloalkyl group, and $Z^1$ is a C1 to C10 alkoxy group, a C1 to C10 haloalkyl group, or a halogen element, provided that $Z^1$ is different from $Y^1$.

The $Ar^1$ may be, for example one of a benzene, a naphthalene, an anthracene, a tetracene, a pentacene, a thiophene, a selenophene, a tellurophene, a furane, a pyrrole, and a fused ring of the foregoing two or more rings. For example, the $Ar^1$ may be a fused ring of two or more rings, for example a naphtalene, an anthracene, a tetracene, a pentacene, a benzothiophene, a dibenzothiophene, a naphthothiophene, a benzonaphthothiophene, a benzoselenophene, a dibenzoselenophene, a naphthoselenophene, a benzonaphthothiophene, a benzotellurophene, a dibenzotellurophene, a naphthotellurophene, a benzonaphthotellurophene, or a combination thereof.

The $Y^1$ may be, for example fluorine (F), chlorine (Cl), bromine (Br), iodine (I), methylfluorine, methylchloride, methylbromine, methyliodine, ethylfluorine, ethylchloride, ethylbromine, or ethyliodine. For example, the $Y^1$ may be bromine (Br), methylbromine, or ethylbromine.

The $Z^1$ may be different from the $Y^1$, and may be, for example methoxy, ethoxy, propoxy, isopropoxy, fluorine (F), chlorine (Cl), bromine (Br), iodine (I), methylfluorine, methylchloride, methylbromine, methyliodine, ethylfluorine, ethylchloride, ethylbromine, or ethyliodine. For example, the $Z^1$ may be methoxy or ethoxy.

The metal alkyl chalcogenide may be, for example metal alkylselenide or metal alkyltelluride, wherein metal may be, for example an alkali metal such as lithium (Li), sodium (Na) or potassium (K), an alkaline-earth metal such as beryllium (Be), magnesium (Mg) or calcium (Ca), or a transition metal such as copper (Cu).

For example, the metal alkyl chalcogenide may be obtained from an alkyl chalcogenide and a metal salt.

The alkyl chalcogenide may be, for example methylselenide, dimethylselenide, dimethyldiselenide, ethylselenide, diethylselenide, diethyldiselenide, methylethylselenide, methylethyldiselenide, propylselenide, dipropylselenide, dipropyldiselenide, methyltelluride, dimethyltelluride, dimethylditelluride, ethyltelluride, diethyltelluride, diethylditelluride, methylethyltelluride, methylethylditelluride, propyltelluride, dipropyltelluride or dipropylditelluride, but is not limited thereto.

The metal salt may be, for example at least one of $NaBH_4$ and $LiAlH_4$, but is not limited thereto.

For example, the metal alkyl chalcogenide may be obtained from a chalcogen element selected from Se and Te and a metal salt.

The metal salt may be, for example at least one of methyl lithium ($LiCH_3$) and methyl magnesium bromide ($CH_3MgBr$), but is not limited thereto.

The first intermediate may be obtained in the presence of a palladium catalyst and a tertiary phosphine catalyst.

The palladium catalyst may include, for example tris (dibenzylideneacetone)dipalladium(0), but is not limited thereto.

The tertiary phosphine catalyst may include a metal-free tertiary phosphine catalyst and the metal-free tertiary phosphine catalyst may be, for example represented by Chemical Formula 5.

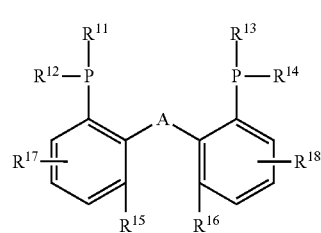

[Chemical Formula 5]

In Chemical Formula 5,

A is a single bond, a substituted or unsubstituted C1 to C3 alkylene group, or oxygen (O), $R^{11}$ to $R^{14}$ are independently a substituted or unsubstituted C6 to C12 aryl group or a substituted or unsubstituted C3 to C12 cycloalkyl group, and $R^{15}$ to $R^{18}$ are independently hydrogen, a substituted or unsubstituted C1 to C10 alkyl group, a substituted or unsubstituted C6 to C20 aryl group, or a substituted or unsubstituted C3 to C20 cycloalkyl group, and $R^{15}$ and $R^{16}$ are independently present or are linked to provide a ring.

The metal-free tertiary phosphine catalyst may include, for example bis[2-(diphenylphosphino)phenyl]methane, bis [2-(diphenylphosphino)phenyl]ether, bis[2-(di-o-tolyphosphino)phenyl]ether, bis[2-(dicyclohexylphosphino)phenyl] ether, 4,6-bis(diphenylphosphino)dibenzofuran, or a combination thereof, but is not limited thereto.

The first intermediate may be obtained by mixing the compound represented by Chemical Formula 1, the metal alkyl chalcogenide, the palladium catalyst, and the tertiary phosphine catalyst in a solvent followed by heat treatment.

The solvent may be, for example an aliphatic hydrocarbon solvent such as hexane and heptane; an aromatic hydrocarbon solvent such as toluene, pyridine, quinoline, anisole, mesitylene, and xylene; a ketone-based solvent such as methyl isobutyl ketone, 1-methyl-2-pyrrolidinone (NMP), cyclohexanone, and acetone; an ether-based solvent such as tetrahydrofuran and isopropyl ether; an acetate-based solvent such as ethyl acetate, butyl acetate, propylene glycol methyl ether acetate; an amide-based solvent such as dimethyl acetamide and dimethyl formamide (DMF); a nitrile-based solvent such as acetonitrile and benzonitrile; and a mixture of the solvents, but is not limited thereto.

The heat treatment may be, for example performed at about 70° C. to 150° C. for about 10 hours to 24 hours, but is not limited thereto.

The first intermediate may be an alkylseleno derivative or an alkyltelluro derivative and, for example represented by Chemical Formula 2.

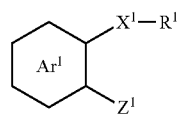

[Chemical Formula 2]

In Chemical Formula 2, $Ar^1$ is one of a substituted or unsubstituted aromatic ring, a substituted or unsubstituted heteroaromatic ring, and a fused ring of the foregoing two or more rings, $Z^1$ is a C1 to C10 alkoxy group, a C1 to C10 haloalkyl group, or a halogen element, $X^1$ is Se or Te, and $R^1$ is a substituted or unsubstituted C1 to O10 alkyl group.

From the first intermediate, a second intermediate having a structure that a chalcogen-containing group and a sulfonate group are substituted at an ortho-position of a ring ($Ar^1$) may be obtained.

The second intermediate may be, for example represented by Chemical Formula 3.

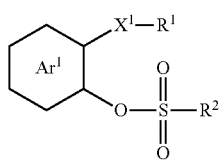

[Chemical Formula 3]

In Chemical Formula 3, $Ar^1$ is one of a substituted or unsubstituted aromatic ring, a substituted or unsubstituted heteroaromatic ring, and a fused ring of the foregoing two or more rings, $X^1$ is Se or Te, $R^1$ is a substituted or unsubstituted C1 to C10 alkyl group, and $R^2$ is hydrogen, a substituted or unsubstituted C1 to C20 alkyl group, a C1 to C20 haloalkyl group, a substituted or unsubstituted C6 to C20 aryl group, a halogen element, or a combination thereof.

The second intermediate has a structure where a chalcogen-containing group and a sulfonate group are substituted at the ortho- of the ring ($Ar^1$) and thus may effectively provide a third intermediate that will be described later.

The second intermediate may be directly obtained from the first intermediate or prepared from a 2' intermediate after first obtaining the 2' intermediate represented by Chemical Formula 3'.

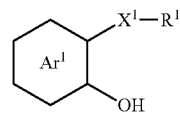

[Chemical Formula 3']

In Chemical Formula 3', $Ar^1$ is one of a substituted or unsubstituted aromatic ring, a substituted or unsubstituted heteroaromatic ring, and a fused ring of the foregoing two or more rings, $X^1$ is Se or Te, and $R^1$ is a substituted or unsubstituted C1 to C10 alkyl group.

The 2' intermediate represented by Chemical Formula 3' may be for example obtained by adding tribromoboron to the first intermediate.

The second intermediate may be for example obtained by supplying the 2' intermediate with a substituted or unsubstituted sulfonic anhydride, wherein the sulfonic anhydride may be for example a methanesulfonic anhydride, for example, a methanesulfonic anhydride substituted with a halogen element, and for example, a trifluoromethanesulfonic anhydride.

The obtaining of the second intermediate may be performed in a solvent, and the solvent may be the same as above without a particular limit.

The second intermediate may be, for example a compound represented by Chemical Formula 3a.

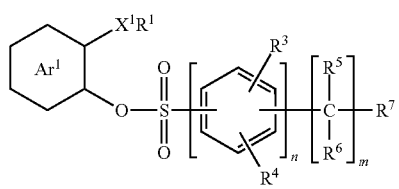

[Chemical Formula 3a]

In Chemical Formula 3a, $Ar^1$ is one of a substituted or unsubstituted aromatic ring, a substituted or unsubstituted heteroaromatic ring, and a fused ring of the foregoing two or more rings, $X^1$ is Se or Te, $R^1$ is a substituted or unsubstituted C1 to C10 alkyl group, $R^3$ to $R^7$ are independently hydrogen, a substituted or unsubstituted C1 to C20 alkyl group, a C1 to C20 haloalkyl group, a substituted or unsubstituted C6 to C20 aryl group, a halogen element, or a combination thereof, n is 0, 1, or 2, and m is an integer of 0 to 10.

The second intermediate may be, for example a compound represented by Chemical Formula 3aa.

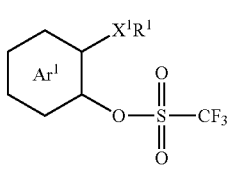

[Chemical Formula 3aa]

In Chemical Formula 3aa, $Ar^1$ is one of a substituted or unsubstituted aromatic ring, a substituted or unsubstituted heteroaromatic ring, and a fused ring of the foregoing two or more rings, $X^1$ is Se or Te, and $R^1$ is a substituted or unsubstituted C1 to C10 alkyl group.

The third intermediate may be obtained from the second intermediate and a compound represented by Chemical Formula 4.

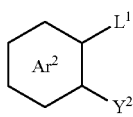

[Chemical Formula 4]

In Chemical Formula 4, $Ar^2$ is one of a substituted or unsubstituted aromatic ring, a substituted or unsubstituted heteroaromatic ring, and a fused ring of the foregoing two or more rings, $Y^2$ is a halogen element or a C1 to C10 haloalkyl group, and $L^1$ is an ethenyl group or an ethynyl group.

The $Ar^2$ may be, for example one of a benzene, a naphthalene, an anthracene, a tetracene, a pentacene, a thiophene, a selenophene, a tellurophene, a furane, a pyrrole, and a fused ring of the foregoing two or more rings. For example, the $Ar^1$ may be a fused ring of two or more rings, for example a naphtalene, an anthracene, a tetracene, a pentacene, a benzothiophene, a dibenzothiophene, a naphthothiophene, a benzonaphthothiophene, a benzoselenophene, a dibenzoselenophene, a naphthoselenophene, a benzonaphthothiophene, a benzotellurophene, a dibenzotellurophene, a naphthotellurophene, a benzonaphthotellurophene, or a combination thereof.

The third intermediate may be, for example represented by Chemical Formula 4a.

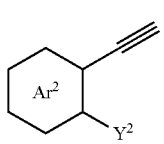

[Chemical Formula 4a]

In Chemical Formula 4a, $Ar^2$ is one of a substituted or unsubstituted aromatic ring, a substituted or unsubstituted heteroaromatic ring, and a fused ring of the foregoing two or more rings, and $Y^2$ is a halogen element or a C1 to C10 haloalkyl group.

The third intermediate may be, for example represented by Chemical Formula 4aa.

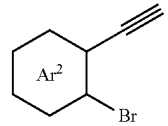

[Chemical Formula 4aa]

In Chemical Formula 4aa, $Ar^2$ is one of a substituted or unsubstituted aromatic ring, a substituted or unsubstituted heteroaromatic ring, and a fused ring of the foregoing two or more rings.

The second intermediate and the compound represented by Chemical Formula 4 may be for example used in a mole ratio of about 1:9 to 9:1, in a mole ratio of about 2:8 to 8:2, in a mole ratio of about 3:7 to 7:3, in a mole ratio of about 4:6 to 6:4, or in a mole ratio of about 5:5.

During the obtaining of the third intermediate, a halogen salt, for example, potassium iodide may be supplied, but is not limited thereto. The halogen salt may help deintercalation of the sulfonate group from the second intermediate and promote a reaction.

In addition, at least one catalyst may be supplied during the obtaining of the third intermediate, and the catalyst may be for example a metal catalyst, for example a copper catalyst such as copper iodide and/or a palladium catalyst such as palladium (0) bis(triphenylphosphine)dichloride, but is not limited thereto.

In addition, a base compound, for example, amine, an amine derivative, and/or cesium carbonate may be supplied during the obtaining of the third intermediate. The amine derivative may be primary amine, secondary amine and/or tertiary amine and, for example, triethylamine, but is not limited thereto.

The obtaining of the third intermediate may be performed by reacting the second intermediate and the compound represented by Chemical Formula 4 with the catalyst in the solvent. The solvent may be the same as above without a particular limit.

The third intermediate may be, for example represented by Chemical Formula 6.

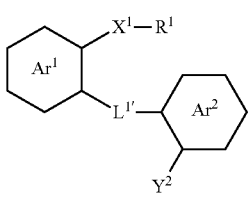

[Chemical Formula 6]

In Chemical Formula 6, $Ar^1$ and $Ar^2$ are independently one of a substituted or unsubstituted aromatic ring, a substituted or unsubstituted heteroaromatic ring, and a fused ring of the foregoing two or more rings, $X^1$ is Se or Te, $R^1$ is a substituted or unsubstituted C1 to C10 alkyl group, $Y^2$ is a halogen element or a C1 to C10 haloalkyl group, and $L^{1'}$ is an ethenylene group or an ethynylene group.

The third intermediate may be, for example represented by Chemical Formula 6a.

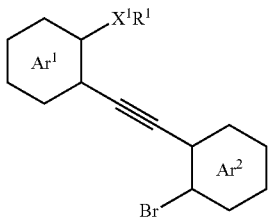

[Chemical Formula 6a]

In Chemical Formula 6a, $Ar^1$ and $Ar^2$ are independently one of a substituted or unsubstituted aromatic ring, a substituted or unsubstituted heteroaromatic ring, and a fused ring of the foregoing two or more rings, $X^1$ is Se or Te, and $R^1$ is a substituted or unsubstituted C1 to C10 alkyl group.

A fourth intermediate including a chalcogen-containing ring may be obtained by ring-closure of the third intermediate. The fourth intermediate may include for example a selenophene ring or a tellurophene ring.

The fourth intermediate may be prepared by supplying the third intermediate with a halogen molecule. The halogen molecule may be for example an iodine molecule ($I_2$), but is not limited thereto.

The obtaining of the fourth intermediate may be performed in a solvent, but the solvent may be the same as above without a particular limit.

The fourth intermediate may be, for example represented by Chemical Formula 7.

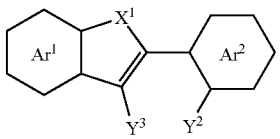

[Chemical Formula 7]

In Chemical Formula 7, $Ar^1$ and $Ar^2$ are independently one of a substituted or unsubstituted aromatic ring, a substituted or unsubstituted heteroaromatic ring, and a fused ring of the foregoing two or more rings, $X^1$ is Se or Te, and $Y^2$ and $Y^3$ are independently a halogen element or a C1 to C10 haloalkyl group.

The fourth intermediate may be, for example represented by Chemical Formula 7a.

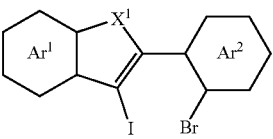

[Chemical Formula 7a]

In Chemical Formula 7a, $Ar^1$ and $Ar^2$ are independently one of a substituted or unsubstituted aromatic ring, a substituted or unsubstituted heteroaromatic ring, and a fused ring of the foregoing two or more rings, and $X^1$ is Se or Te.

The fourth intermediate may be formed into a fused heteroaromatic compound having chalcogen elements through supply of the chalcogen elements and a catalytic cyclization reaction.

The chalcogen elements may be the same as or different from chalcogen elements included in the first intermediate and, for example sulfur (S), selenium (Se), tellurium (Te), or oxygen (O).

The fused heteroaromatic compound may be for example prepared by using a copper agent such as copper iodide and Cu(OTf) (copper trifluoromethanesulfonate), a palladium agent such as Pd(PPh$_3$)$_4$, and/or a metal catalyst prepared by combining with a phosphine ligand such as 1,1'-bis(diphenylphosphino)ferrocene (dppf) or bis[2-(diphenylphosphino)phenyl]ether (DPEPhos), but is not limited thereto.

In addition, the fused heteroaromatic compound may be for example prepared by supplying an inorganic base such as potassium carbonate ($K_2CO_3$) or an organic base such as triisopropylamine, but is not limited thereto.

The preparation of the fused heteroaromatic compound may be performed in a solvent, and the solvent may be the same as above without a particular limit.

The fused heteroaromatic compound may be, for example represented by Chemical Formula 8.

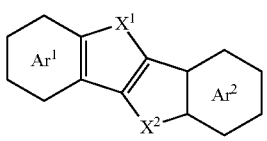

[Chemical Formula 8]

In Chemical Formula 8, $Ar^1$ and $Ar^2$ are independently one of a substituted or unsubstituted aromatic ring, a substituted or unsubstituted heteroaromatic ring, and a fused ring of the foregoing two or more rings, $X^1$ is Se or Te, and $X^2$ is O, S, Se, or Te.

For example, the fused heteroaromatic compound may be represented by one of Chemical Formulae 8a to 8g, but is not limited thereto.

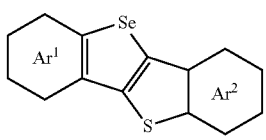

[Chemical Formula 8a]

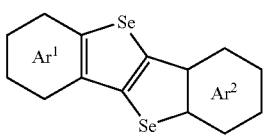

[Chemical Formula 8b]

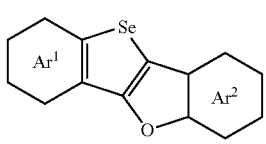

[Chemical Formula 8c]

-continued

[Chemical Formula 8d]
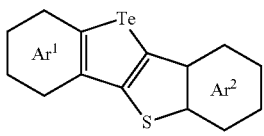

[Chemical Formula 8e]
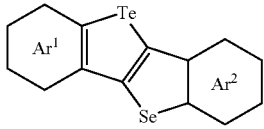

[Chemical Formula 8f]
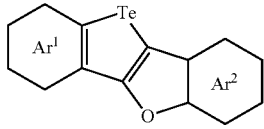

[Chemical Formula 8g]
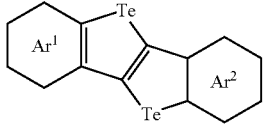

In Chemical Formulae 8a to 8g, $Ar^1$ and $Ar^2$ are independently one of a substituted or unsubstituted aromatic ring, a substituted or unsubstituted heteroaromatic ring, and a fused ring of the foregoing two or more rings.

$Ar^1$ and $Ar^2$ may be, for example independently one of a benzene, a naphthalene, an anthracene, a tetracene, a pentacene, a thiophene, a selenophene, a tellurophene, a furane, a pyrrole, and a fused ring of the foregoing two or more rings. For example, $Ar^1$ and $Ar^2$ may be, for example independently a fused ring of two or more rings, for example a naphtalene, an anthracene, a tetracene, a pentacene, a benzothiophene, a dibenzothiophene, a naphthothiophene, a benzonaphthothiophene, a benzoselenophene, a dibenzoselenophene, a naphthoselenophene, a benzonaphthothiophene, a benzotellurophene, a dibenzotellurophene, a naphthotellurophene, a benzonaphthotellurophene, or a combination thereof.

The fused heteroaromatic compound has, for example a structure where four or more aromatic rings and/or heteroaromatic rings are fused, and may have a uniform and stable oxidation potential when applied to an electronic device such as an organic thin film transistor due to a compact planar molecular structure, and show high charge mobility since the intermolecular packing and stacking are improved. Therefore, it may be effectively applied to an electron transporting material such as a semiconductor.

The fused heteroaromatic compound may have, for example a structure where five or more aromatic rings and/or heteroaromatic rings may be fused, six or more aromatic rings and/or heteroaromatic rings may be fused, seven or more aromatic rings and/or heteroaromatic rings may be fused, or eight or more aromatic rings and/or heteroaromatic rings may be fused.

The fused heteroaromatic compound may have, for example a molecular weight of about 300 to about 3000, or about 300 to about 1500.

The fused heteroaromatic compound may be, for example a compound represented by one of Chemical Structures (1) to (16), but is not limited thereto.

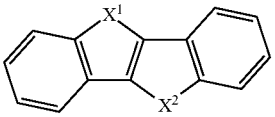
(1)

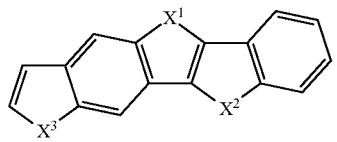
(2)

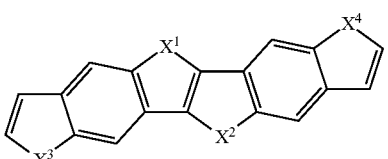
(3)

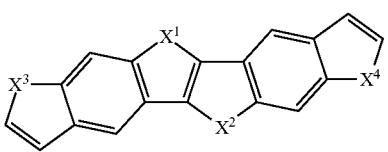
(4)

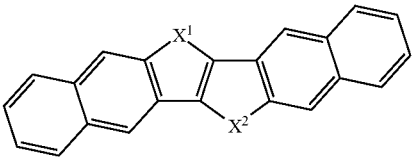
(5)

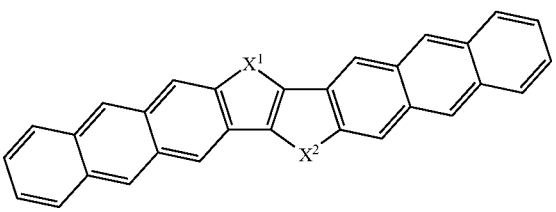
(6)

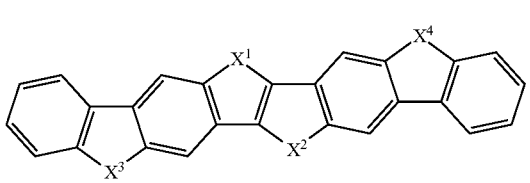
(7)

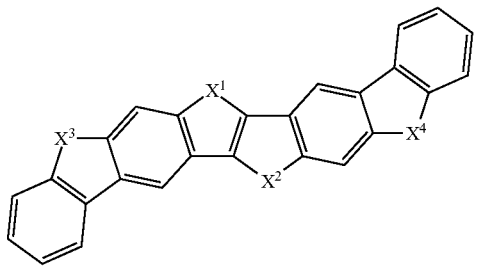
(8)

(9)
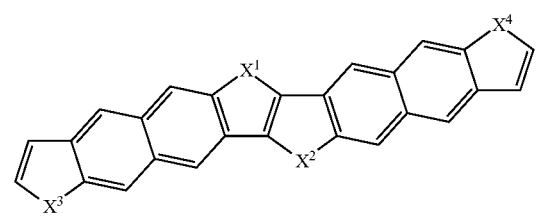

(10)
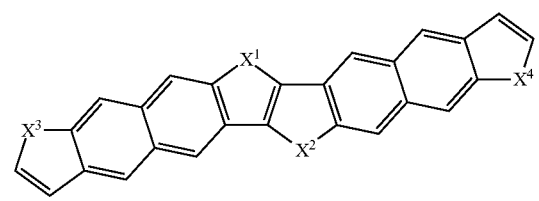

(11)
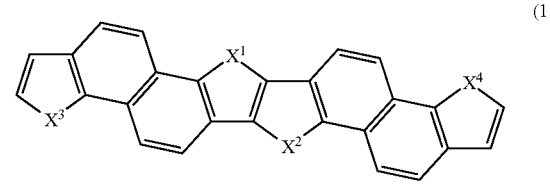

(12)
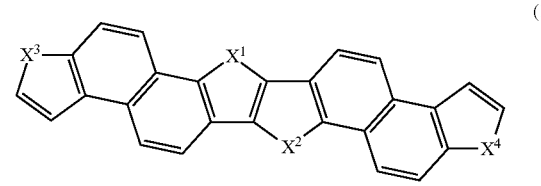

(13)
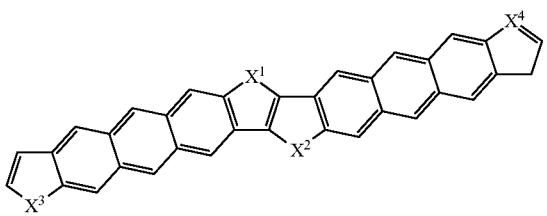

(14)
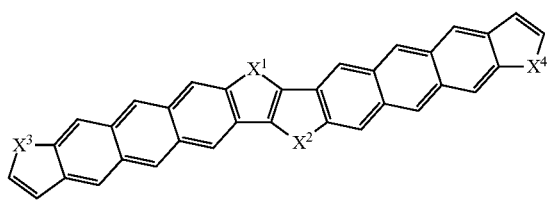

(15)
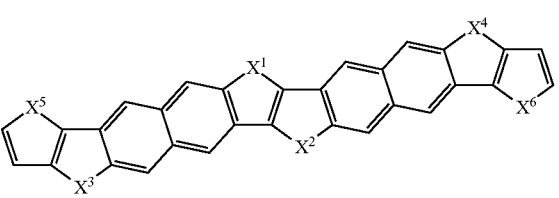

(16)
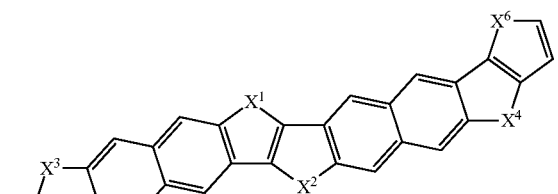

In Chemical Structures (1) to (16),
one of $X^1$ and $X^2$ is selenium (Se) or tellurium (Te),
the other of $X^1$ and $X^2$ is sulfur (S), selenium (Se), tellurium (Te), or oxygen (O), and
$X^3$ to $X^6$ are independently sulfur (S), selenium (Se), tellurium (Te), oxygen (O), or $NR^7$, wherein $R^7$ is hydrogen, a C1 to C10 alkyl group, or a C6 to C30 aryl group.

In Chemical Structures (1) to (16), each aromatic ring and/or heteroaromatic ring may be, for example substituted with at least one substituent, for example a C1 to 010 alkyl group or a C6 to C30 aryl group.

The fused heteroaromatic compound may be, for example one of compounds of Group 1, but is not limited thereto.

[Group 1]

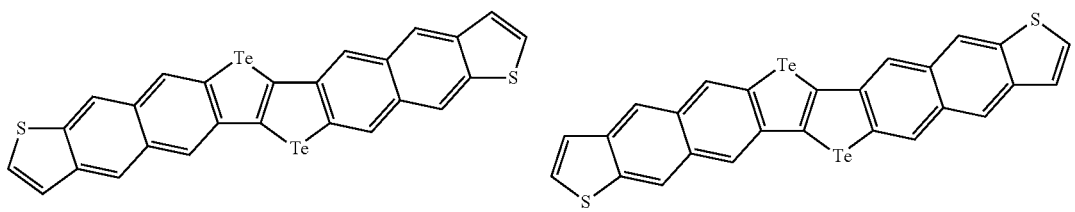

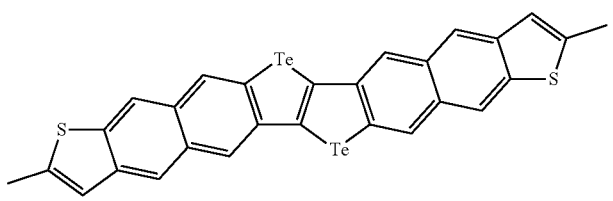

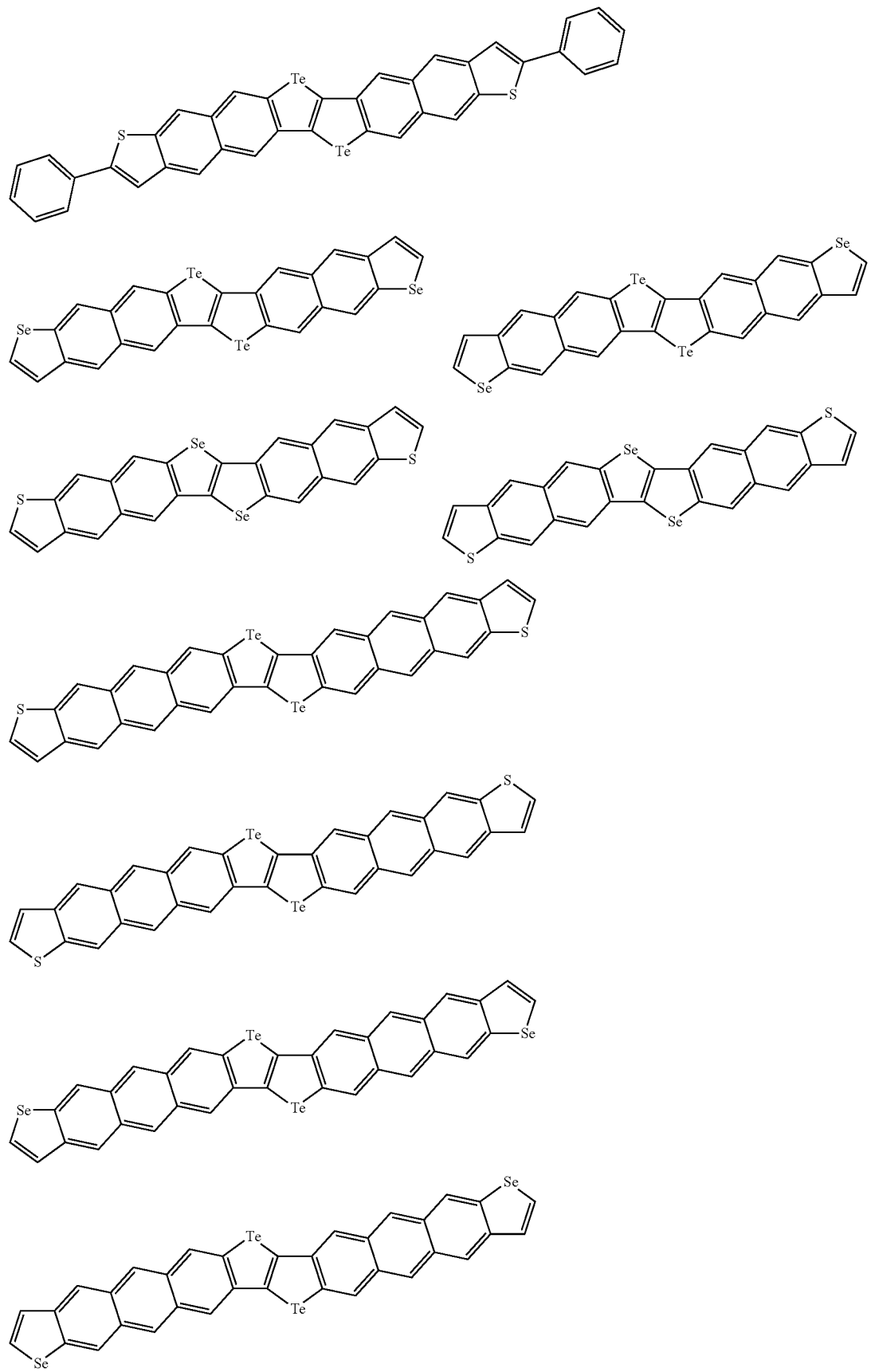

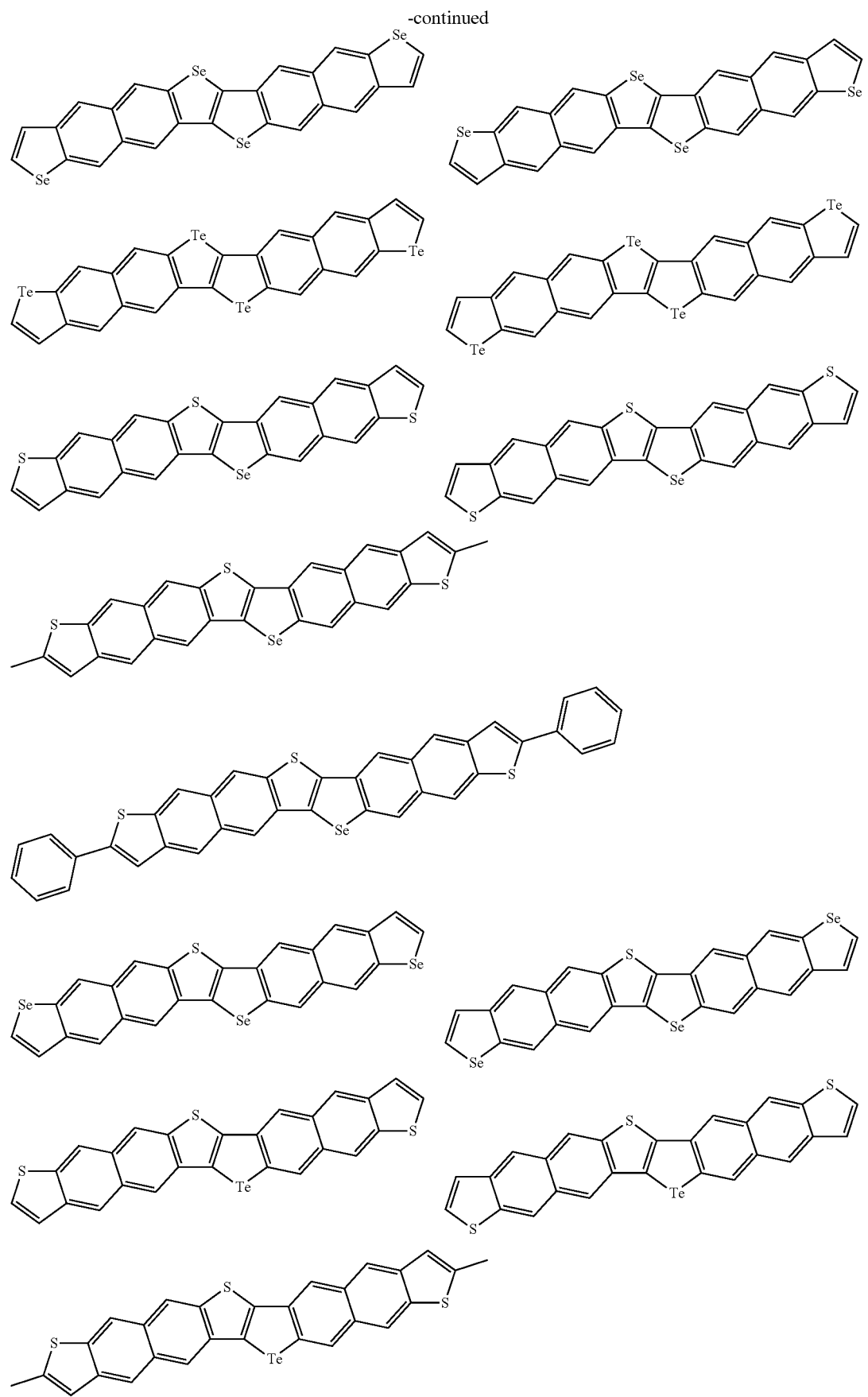

-continued
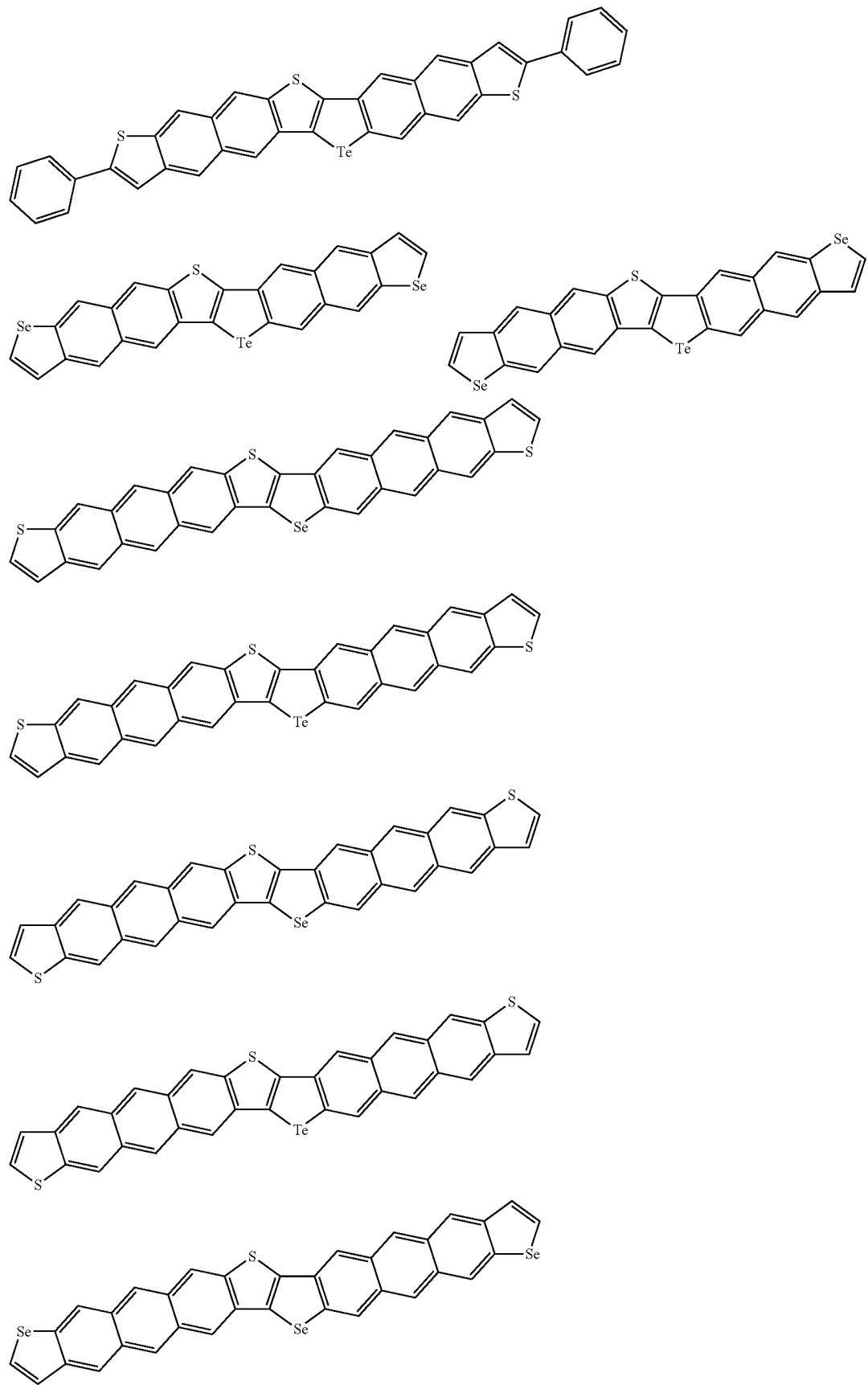

-continued

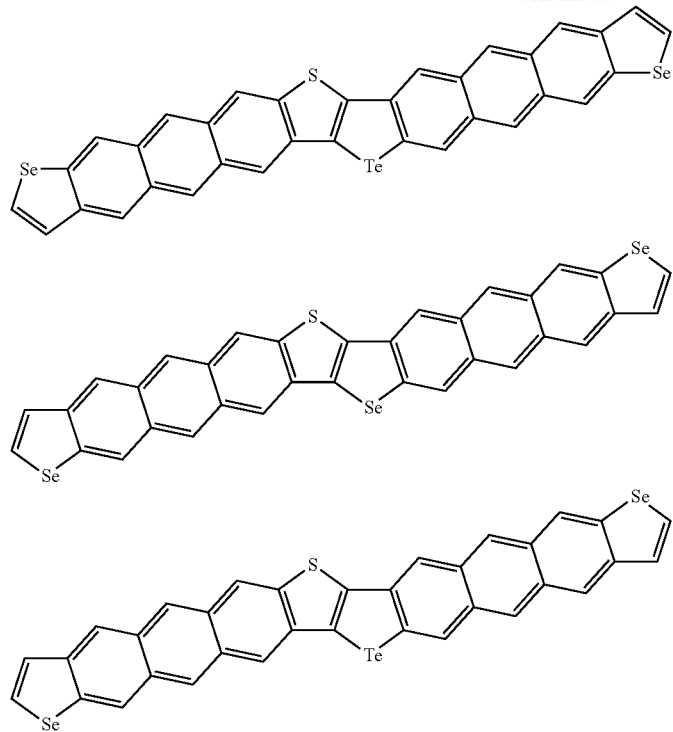

The synthetic method of a fused heteroaromatic compound may use simple synthesis operations and may provide a product with a high yield. The synthetic method may be performed at a relatively low temperature of, for example about 40° C. to about 200° C., for example about 40° C. to about 100° C. The synthetic method may be performed at a relatively short time, and may shorten a time of a conventional method by a half or greater. The synthetic method may provide intermediates and a final product with a high yield, and for example each intermediate and final product may be produced with a yield of about 70% or more, for example about 80% or more.

The fused heteroaromatic compound may be formed into an organic thin film by a deposition or solution process. The organic thin film may be applied to various devices including an organic semiconductor. For example, the fused heteroaromatic compound may be applied to an organic thin film transistor, and may be applied to a charge transport layer and/or an active layer of an electronic device such as a solar cell, an organic light emitting diode (OLED) display, and an organic sensor.

Hereinafter, one example of an organic thin film transistor including the fused heteroaromatic compound is described referring to the drawing.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

A cross-sectional view showing an organic thin film transistor according to some example embodiments is shown.

A gate electrode 124 is formed on a substrate 110 made of transparent glass, silicon, or plastic. The gate electrode 124 is connected to a gate line (not shown) transferring a gate signal. The gate electrode 124 may be made of gold (Au), copper (Cu), nickel (Ni), aluminum (Al), molybdenum (Mo), chromium (Cr), tantalum (Ta), titanium (Ti), an alloy thereof, or a combination thereof.

A gate insulating layer 140 is formed on the gate electrode 124. The gate insulating layer 140 may be made of an organic material or an inorganic material. Examples of the organic material may include a soluble polymer compound such as a polyvinyl alcohol-based compound, a polyimide-based compound, a polyacryl-based compound, a polystyrene-based compound, and benzocyclobutane (BCB), and examples of the inorganic material may include a silicon nitride (SiNx) and a silicon oxide ($SiO_2$).

A source electrode 173 and a drain electrode 175 are formed on the gate insulating layer 140. The source electrode 173 and the drain electrode 175 face each other with the gate electrode 124 therebetween. The source electrode 173 is electrically connected to the data line (not shown) transferring the data signal. The source electrode 173 and the drain electrode 175 may include at least one metal selected from gold (Au), copper (Cu), nickel (Ni), aluminum (Al), molybdenum (Mo), chromium (Cr), tantalum (Ta), titanium (Ti), an alloy thereof, or a combination thereof.

An organic semiconductor 154 is formed on the source electrode 173 and the drain electrode 175. The organic semiconductor 154 may be made of the fused heteroaromatic compound. The organic semiconductor 154 may be formed in a solution process such as spin coating, slit coating, or inkjet printing by preparing the fused heteroaromatic compound as a solution. However, the fused heteroaromatic compound may be formed using a dry process such as deposition.

Although the bottom gate structured organic thin film transistor is provided as an example of an organic thin film transistor, inventive concepts are not limited thereto, and may be applied to all organic thin film transistors such as a top gate structured organic thin film transistor.

The organic thin film transistor may be applied to a switch or driving device of various electronic devices, and the electronic device may be, for example, a liquid crystal display (LCD), an organic light emitting diode (OLED) display, an eletrophoretic display device, or an organic sensor.

Hereinafter, the present disclosure is illustrated in more detail with reference to examples. However, these examples are non-limiting, and inventive concepts are not limited thereto.

Synthesis of Fused Heteroaromatic Compound

Synthesis Example 1

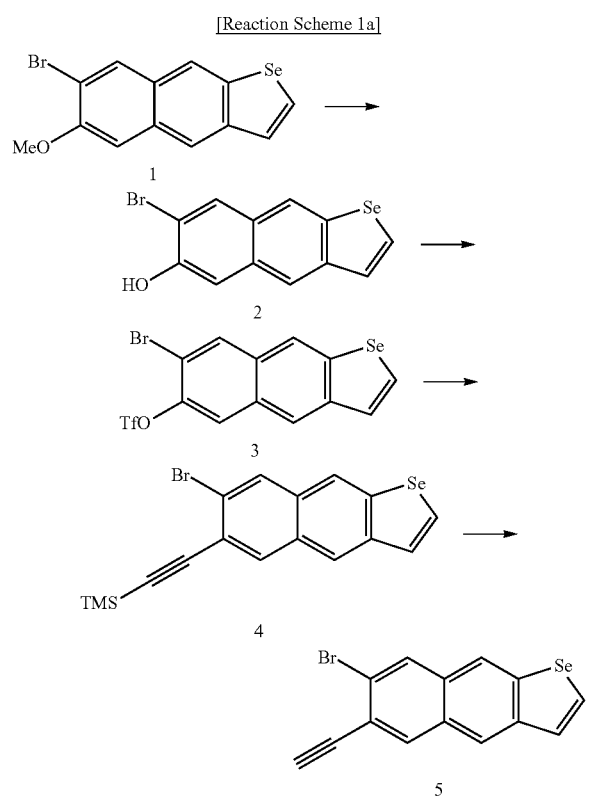

Synthesis of Compound 2

Compound 1 (6.8 g, 20 mmol) is put in a flask, and 400 ml of dichloromethane (CH$_2$Cl$_2$) is added thereto. After lowering a temperature, a 1.0 M tribromoboron solution (BBr$_3$) (26 ml, 20 mmol) is added thereto, and the mixture is stirred for 4 hours. A saturated ammonium chloride solution is added to the reaction solution, and chloroform is added thereto for an extraction. Magnesium sulfate (MgSO$_4$) is added thereto to remove moisture, an extract therein is filtered, and a solvent is removed therefrom to obtain a yellow solid Compound 2. (a yield: 30%)

$^1$H NMR (CDCl$_3$, 300 MHz) 5.59 (s, 1H), 7.49 (s, 1H), 7.59 (d, 1H), 8.00 (d, 1H), 8.08 (s, 1H), 8.17 (s, 1H), 8.24 (s, 1H)

Synthesis of Compound 3

Compound 2 (1.8 g, 5.5 mmol) is put in a flask, and dichloromethane (CH$_2$Cl$_2$, 90 mL) is added thereto to dissolve it. Subsequently, triethylamine (NEt$_3$) (2.1 mL, 15 mmol) is added thereto, then, trifluoromethanesulfonic anhydride (Tf$_2$O, 1.2 mL, 7.2 mmol) is added thereto at 0° C., and the obtained mixture is stirred overnight. Then, a saturated ammonium chloride solution and water are added thereto. Then, a water layer is separated and extracted with dichloromethane. Then, an organic layer is cleaned with a saline solution, dried and concentrated with anhydrous magnesium sulfate, and then, purified through column chromatography to obtain Compound 3. (a yield: 48%)

$^1$H NMR (CDCl$_3$, 300 MHz) 7.67 (d, 1H), 7.94 (s, 1H), 8.12 (d, 1H), 8.22 (s, 1H), 8.32 (s, 1H), 8.37 (s, 1H)

Synthesis of Compounds 4 and 5

Compound 3 (4.3 g, 7.4 mmol), dimethyl formamide (DMF) (100 mL), and triethylamine (NEt$_3$) (7.8 mL, 56 mmol) are put in a flask. Subsequently, trimethylsilylacetylene (TMSA) (1.3 mL, 7.4 mmol), copper iodide (53 mg, 0.28 mmol), and palladium bis(triphenylphosphine)dichloride (Pd(PPh$_3$)$_2$Cl$_2$) (197 mg, 0.28 mmol) are added thereto, and the mixture is stirred overnight. Then, a saturated ammonium chloride solution and water are added thereto, and a water layer is extracted with dichloromethane. Then, an organic layer therefrom is cleaned with a silane solution, dried with anhydrous magnesium sulfate, and purified through column chromatography to obtain Compound 4. Then, Compound 4 is suspended in methanol (MeOH) (100 mL), and potassium hydroxide (KOH) (0.83 g, 14.8 mmol) is added thereto. Then, the obtained mixture is stirred for 4 hours to precipitate and obtain solid Compound 5. (a yield: 87%)

$^1$H NMR (CDCl$_3$, 300 MHz) 3.42 (s, 1H), 7.64 (d, 1H), 8.04 (d, 1H), 8.13 (s, 1H), 8.20 (s, 1H), 8.24 (s, 1H), 8.29 (s, 1H)

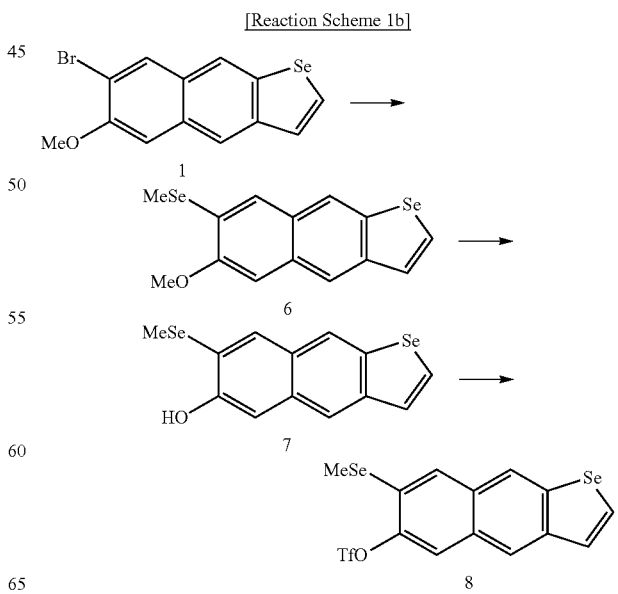

Synthesis of Compound 6 (First Intermediate)

Potassium carbonate (3.1 g, 22 mmol) is put in a flask substituted with nitrogen, and ethanol (80 mL) is added thereto. Dimethyl diselenide ($CH_3SeSeCH_3$) (1.0 mL, 10 mmol) is added thereto, and the obtained mixture is cooled down to 0° C. Sodium borohydride ($NaBH_4$) (0.84 g, 22 mmol) is added thereto, and the obtained mixture is stirred at 0° C. for 30 minutes and additionally at room temperature for 30 minutes. Toluene (100 mL) is added thereto, the mixture is heated at 120° C. to remove ethanol, and Compound 1 (5.0 g, 15 mmol), tris(dibenzylideneacetone) dipalladium (0) (1.35 g, 1.47 mmol), and bis[2-(diphenylphosphino)phenyl]ether (1.58 g, 2.94 mmol) are added thereto. After adding the toluene (200 mL) thereto, the mixture is heated at 110° C. for 19 hours. Then, the mixture is cooled down, dried with sodium bicarbonate, and filtered, and an organic solvent therein is vacuum-removed. A product therefrom is purified through silica gel column (a solvent: chloroform hexane) to obtain white solid Compound 6. (a yield: 60%)

$^1$H NMR ($CDCl_3$, 300 MHz) 2.41 (s, 3H), 4.02 (s, 3H), 7.15 (s, 1H), 7.59 (s, 1H), 7.61 (m, 2H), 7.95 (d, 1H), 8.18 (s, 1H), 8.24 (s, 1H)

Synthesis of Compound 7

Compound 6 (3.3 g, 9.3 mmol) is put in a flask, and dichloromethane (400 ml) is added thereto. After lowering a temperature, a 1.0 M tribromoboron ($BBr_3$) solution (12 ml, 12 mmol) is added thereto, and the mixture is stirred for 4 hours. A saturated ammonium chloride solution is added to the reaction solution, and chloroform is added thereto for an extraction. After adding $MgSO_4$ thereto to remove moisture, an extract therefrom is filtered, and a solvent is removed therefrom to obtain yellow solid Compound 7. (a yield: 87.5%)

$^1$H NMR ($CDCl_3$, 300 MHz) 2.29 (s, 3H), 6.49 (s, 1H), 7.43 (s, 1H), 7.59 (d, 1H), 7.98 (d, 1H), 8.17 (s, 2H), 8.26 (s, 1H)

Synthesis of Compound 8 (Second Intermediate)

Compound 7 (2.8 g, 8.2 mmol) is put in a flask, and dichloromethane ($CH_2Cl_2$) (300 mL) is added thereto to dissolve it. Subsequently, triethylamine ($NEt_3$) (3.1 mL, 22.1 mmol) is added thereto, then, trifluoromethane sulfonic anhydride ($Tf_2O$) (1.8 mL, 10.7 mmol) is added thereto at 0° C., and the obtained mixture is stirred overnight. Then, a saturated ammonium chloride solution and water are added thereto. Then, a water layer is separated and extracted with dichloromethane. Then, an organic layer therefrom is cleaned with a silane solution, dried and concentrated with anhydrous magnesium sulfate, and purified through column chromatography to obtain white solid Compound 8. (a yield: 98%)

$^1$H NMR ($CDCl_3$, 300 MHz) 2.49 (s, 3H), 7.64 (d, 1H), 7.85 (s, 1H), 7.89 (s, 1H), 8.06 (d, 1H), 8.29 (s, 1H), 8.36 (s, 1H)

[Reaction Scheme 1c]

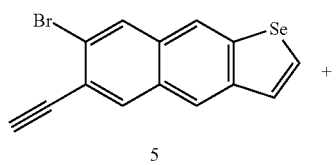

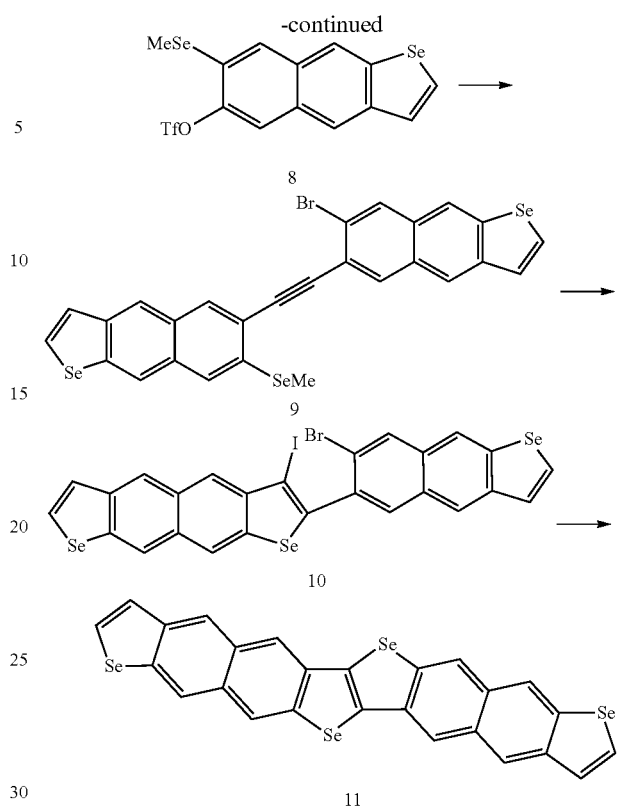

Synthesis of Compound 9 (Third Intermediate)

Compound 8 (1.7 g, 3.59 mmol), copper iodide (CuI) (102 mg, 76 mmol), palladium (0) bis(triphenylphosphine)dichloride ($Pd(PPh_3)_2Cl_2$) (76 mg, 0.11 mmol), tetrabutylammoniumiodide ($Bu_4NI$) (2.0 g, 5.39 mmol), triethylamine ($NEt_3$) (4.8 mL), and dimethyl formamide (DMF) (24 mL) are put in a flask and stirred for 15 minutes. Subsequently, Compound 5 (1.2 g, 3.59 mmol) is thereto, and the mixture is stirred at 70° C. overnight to precipitate and obtain 2.6 g of solid Compound 9. (a yield: 85%)

$^1$H NMR ($CDCl_3$, 300 MHz) 2.53 (s, 3H), 7.66 (m, 2H), 7.72 (s, 1H), 7.99 (d, 1H), 8.05 (d, 1H), 8.19 (s, 1H), 8.24 (s, 1H), 8.27 (s, 1H), 8.31 (m, 4H)

Synthesis of Compound 10 (Fourth Intermediate)

Compound 9 (1.9 g, 2.9 mmol) and tetrahydrofuran (THF) (400 mL) are put in a flask. Subsequently, iodine ($I_2$) (1.5 g, 5.8 mmol) is added thereto, and the mixture is stirred overnight. Then, methanol is added thereto for an extraction, and an extract therefrom is filtered to obtain Compound 10. (a yield: 95%)

$^1$H NMR ($CDCl_3$, 300 MHz) 7.69 (m, 2H), 8.01 (d, 1H), 8.07 (m, 2H), 8.28 (s, 1H), 8.35 (s, 1H), 8.39 (d, 2H), 8.49 (s, 1H), 8.56 (d, 2H).

Synthesis of Compound 11 (Final Compound)

Compound 10 (2.0 g, 2.6 mmol), copper iodide (CuI) (100 mg, 0.52 mmol), a selenium powder (Se) (0.62 g, 7.8 mmol), and potassium carbonate ($K_2CO_3$) (1.1 g, 7.8 mmol) are put in a flask. Subsequently, N-methylpyrrolidone (NMP) (150 mL) is added thereto, and the mixture is stirred at 120° C.

overnight. After cooling the resultant down to 0° C., a side product is precipitated. Then, the side product is suspended in a mixed solvent of dimethyl acetamide and water, filtered, and then, cleaned with water, acetone, and tetrahydrofuran (THF) to obtain Compound 11. (a yield: 75%)

MS (MALDI-TOF-MS, m/z) 643.76 (M+)

Synthesis Example 2

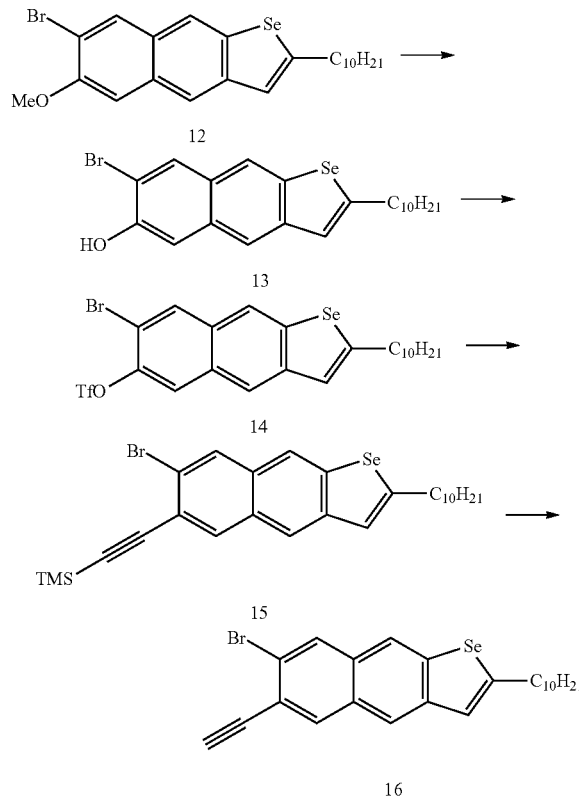

Synthesis of Compound 13

Compound 12 (2.0 g, 4.2 mmol) and dichloromethane ($CH_2Cl_2$) (200 ml) are put in a flask. After lowering a temperature, a 1.0 M tribromoboron solution ($BBr_3$) (4.2 ml, 4.2 mmol) is added thereto, and the mixture is stirred for 4 hours. A saturated ammonium chloride solution is added to the reaction solution, and chloroform is added thereto for an extraction. After adding magnesium sulfate ($MgSO_4$) thereto to remove moisture, an extract therefrom is filtered, and a solvent therein is removed to obtain a yellow solid Compound 13. (a yield: 100%)

$^1$H NMR ($CDCl_3$, 300 MHz) 0.88 (t, 3H), 1.26 (m, 14H), 1.75 (m, 2H), 2.94 (t, 2H), 5.56 (s, 1H), 7.18 (s, 1H), 7.43 (s, 1H), 7.95 (s, 1H), 8.01 (s, 1H), 8.10 (s, 1H)

Synthesis of Compound 14

Compound 13 (1.8 g, 3.9 mmol) is dissolved in dichloromethane ($CH_2Cl_2$) (90 mL) in a flask. Subsequently, triethylamine ($NEt_3$) (1.5 mL, 10.5 mmol) is added thereto, trifluoromethanesulfonic anhydride ($Tf_2O$) (0.86 mL, 5.1 mmol) is added thereto at 0° C., and the mixture is stirred overnight. Subsequently, a saturated ammonium chloride solution and water are added thereto. Then, a water layer is separated and extracted with dichloromethane. Subsequently, an organic layer therefrom is cleaned with a silane solution, dried and concentrated with anhydrous magnesium sulfate, and purified through column chromatography to obtain Compound 14. (a yield: 100%)

$^1$H NMR ($CDCl_3$, 300 MHz) 0.88 (t, 3H), 1.27 (m, 14H), 1.77 (m, 2H), 2.97 (t, 2H), 7.87 (s, 1H), 8.10 (s, 1H), 8.16 (s, 1H), 8.22 (s, 1H)

Synthesis of Compounds 15 and 16

Compound 14 (2.3 g, 3.8 mmol), dimethyl formamide (DMF) (50 mL), and triethylamine ($NEt_3$) (3.2 mL, 23 mmol) are put in a flask. Subsequently, trimethylsilylacetylene (TMSA) (0.54 mL, 3.8 mmol), copper iodide (21 mg, 0.11 mmol), and palladium bis(triphenylphosphine)dichloride ($Pd(PPh_3)_2Cl_2$) (77 mg, 0.11 mmol) are added thereto, and the mixture is stirred overnight. Subsequently, a saturated ammonium chloride solution and water are added thereto, and a water layer is extracted with dichloromethane. Then, an organic layer therefrom is cleaned with a silane solution, dried with anhydrous magnesium sulfate, and purified through column chromatography to obtain Compound 15. Subsequently, Compound 15 is suspended in methanol (MeOH) (100 mL), and potassium hydroxide (KOH) (0.83 g, 14.8 mmol) is added thereto. The obtained mixture is stirred for 4 hours, and water is added thereto to precipitate and obtain solid Compound 16. (a yield: 81%)

*341$^1$H NMR ($CDCl_3$, 300 MHz) 0.88 (t, 3H), 1.27 (m, 14H), 1.76 (m, 2H), 2.95 (t, 2H), 3.40 (s, 1H), 7.23 (s, 1H), 8.02 (s, 1H), 8.07 (s, 1H), 8.14 (s, 1H), 8.16 (s, 1H)

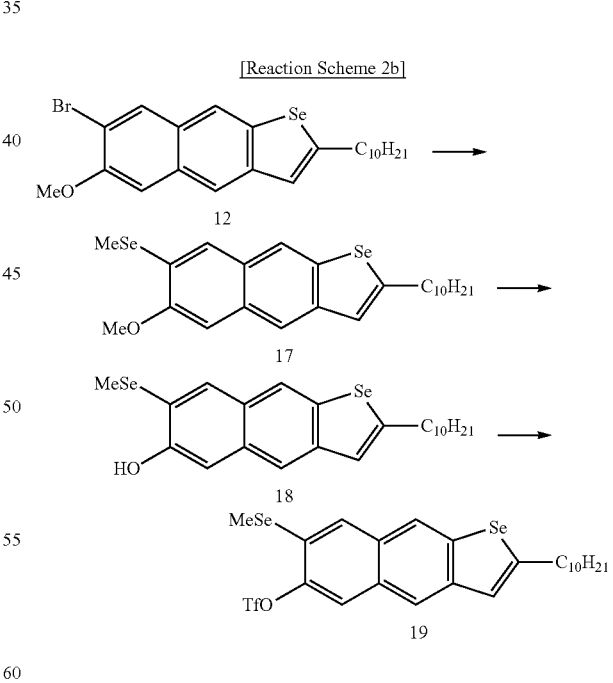

Synthesis of Compound 17 (First Intermediate)

Potassium carbonate (0.9 g, 6.3 mmol) is put in a flask substituted with nitrogen, and 140 mL of ethanol is added thereto. Dimethyl diselenide ($CH_3SeSeCH_3$) (0.29 mL, 2.9 mmol) is added thereto, and the mixture is cooled down to 0° C. Sodium borohydride (NaBH$_4$) (0.24 g, 16.3 mmol) is added thereto, and the obtained mixture is stirred at 0° C. for 30 minutes and additionally at room temperature for 30 minutes. 30 mL of toluene is added thereto, the mixture is heated at 120° C. to remove ethanol, and then, Compound 12 (2.0 g, 4.2 mmol), tris(dibenzylideneacetone) dipalladium (0) (0.38 g, 0.42 mmol), and bis[2-(diphenylphosphino)phenyl]ether (0.45 g, 0.84 mmol) are added thereto. Toluene (200 mL) is added thereto, and the mixture is heated at 110° C./19 hours. After lowering the temperature, the resultant is dried with sodium bicarbonate and filtered, and an organic solvent is vacuum-removed. A product therefrom is purified through silica gel column (a solvent: hexanechloroform) to obtain white solid Compound 17. (a yield: 36%)

$^1$H NMR (CDCl$_3$, 300 MHz) 0.90 (t, 3H), 1.27 (m, 14H), 1.75 (m, 2H), 2.39 (s, 3H), 2.94 (t, 2H), 4.00 (s, 1H), 7.10 (s, 1H), 7.19 (s, 1H), 7.55 (s, 1H), 7.97 (s, 1H), 8.11 (s, 1H)

Synthesis of Compound 18

Compound 17 (1.4 g, 2.8 mmol) and dichloromethane (120 ml) are put in a flask. After lowering a temperature, a 1.0 M tribromoboron (BBr$_3$) solution (4.2 ml, 4.2 mmol) is added thereto, and the mixture is stirred for 4 hours. A saturated ammonium chloride solution is added to the reaction solution, and chloroform is added thereto for an extraction. After adding MgSO$_4$ thereto to remove moisture, the resultant is filtered, and a solvent is removed to obtain yellow solid Compound 18. (a yield: 87.5%)

$^1$H NMR (CDCl$_3$, 300 MHz) 0.88 (t, 3H), 1.27 (m, 14H), 1.75 (m, 2H), 2.28 (s, 3H), 2.94 (t, 2H), 6.48 (s, 1H), 7.18 (s, 1H), 7.38 (s, 1H), 7.95 (s, 1H), 8.12 (s, 1H)

Synthesis of Compound 19 (Second Intermediate)

Compound 18 (1.33 g, 2.96 mmol) is dissolved in dichloromethane (CH$_2$Cl$_2$) (120 mL) in a flask. Subsequently, triethylamine (NEt$_3$) (1.0 mL, 7.5 mmol) is added thereto, trifluoromethanesulfonic anhydride (Tf$_2$O) (0.6 mL, 3.6 mmol) is added thereto at 0° C., and the mixture is additionally stirred overnight. Then, a saturated ammonium chloride solution and water are added thereto. Subsequently, a water layer is separated and extracted with dichloromethane. Then, an organic layer therefrom is cleaned with a silane solution, dried and concentrated with anhydrous magnesium sulfate, and purified through column chromatography to obtain white solid Compound 19. (a yield: 66%)

$^1$H NMR (CDCl$_3$, 300 MHz) 0.88 (t, 3H), 1.27 (m, 14H), 1.74 (m, 2H), 2.47 (s, 3H), 2.97 (t, 2H), 7.24 (s, 1H), 7.79 (s, 1H), 7.87 (s, 1H), 8.08 (s, 1H), 8.22 (s, 1H)

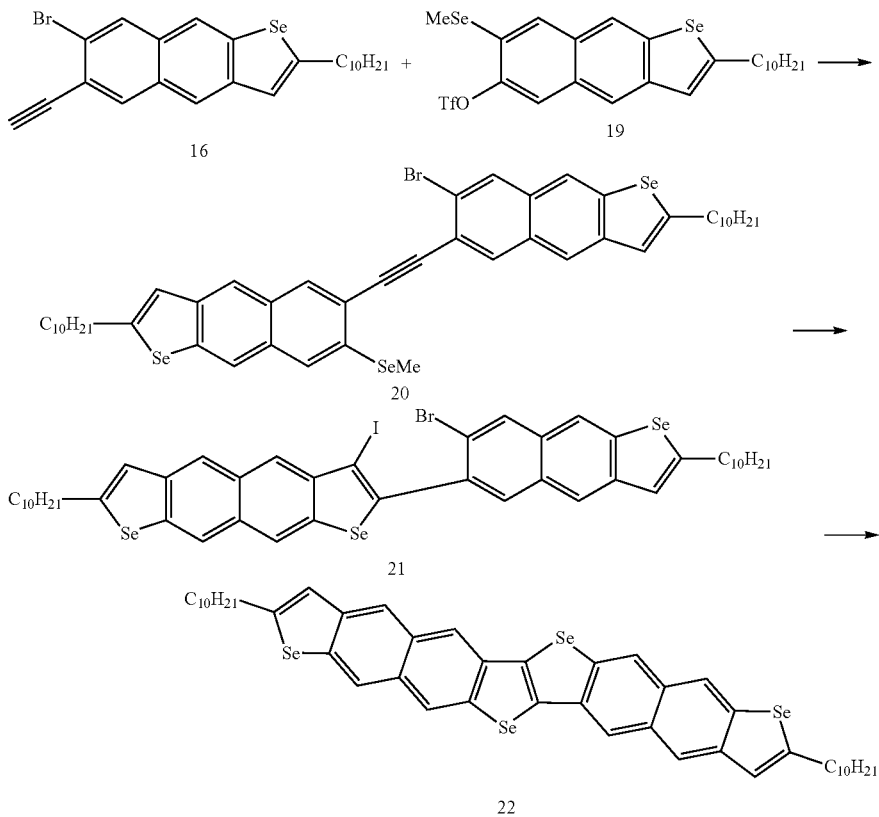

Synthesis of Compound 20 (Third Intermediate)

Compound 19 (1.1 g, 1.8 mmol), copper iodide (CuI) (51 mg, 0.27 mmol), palladium (0) bis(triphenylphosphine) dichloride (Pd(PPh$_3$)$_2$Cl$_2$) (38 mg, 154 mmol), tetrabutylammoniumiodide (Bu$_4$NI) (1.0 g, 2.7 mmol), triethylamine (NEt$_3$) (5 mL), and dimethyl formamide (DMF) (25 mL) are put in a flask and stirred for 15 minutes. Subsequently, Compound 16 (0.85 g, 1.8 mmol) is added thereto, and the obtained mixture is stirred at 70° C. overnight to precipitate and obtain 2.6 g of solid Compound 20. (a yield: 88%)

$^1$H NMR (CDCl$_3$, 300 MHz) 0.88 (t, 6H), 1.27 (m, 28H), 1.77 (m, 4H), 2.51 (s, 3H), 2.96 (t, 4H), 7.23 (s, 1H), 7.25 (s, 1H), 7.67 (s, 1H), 8.05 (s, 1H), 8.07 (s, 1H), 8.12 (s, 1H), 8.17 (m, 3H), 8.26 (s, 1H)

Synthesis of Compound 21 (Fourth Intermediate)

Compound 20 (1.5 g, 1.6 mmol) and tetrahydrofuran (THF) (200 mL) are put in a flask. Subsequently, iodine (I$_2$) (0.81 g, 3.2 mmol) is added thereto, and the mixture is stirred overnight. Then, methanol is added thereto for an extraction, and an extract therefrom is filtered to obtain Compound 21. (a yield: 88%)

$^1$H NMR (CDCl$_3$, 300 MHz) 0.88 (t, 6H), 1.27 (m, 28H), 1.77 (m, 4H), 2.98 (m, 4H), 7.21 (s, 1H), 7.28 (s, 1H), 8.02 (s, 1H), 8.13 (s, 1H), 8.22 (s, 1H), 8.26 (s, 1H), 8.32 (s, 1H), 8.35 (d, 2H), 8.49 (s, 1H)

Synthesis of Compound 22 (Final Compound)

Compound 21 (1.5 g, 1.4 mmol), copper iodide (CuI) (53 mg, 0.28 mmol), a selenium powder (Se) (0.34 g, 4.3 mmol), and potassium carbonate (K$_2$CO$_3$) (0.59 g, 4.3 mmol) are put in a flask. Subsequently, N-methylpyrrolidone (NMP) (100 mL) is added thereto, and the mixture is stirred overnight at 120° C. The resultant is cooled down to 0° C. to precipitate a side product. Subsequently, the side product is suspended in a mixed solvent of dimethyl acetamide and water, filtered, and cleaned with water, acetone, and tetrahydrofuran (THF) to obtain Compound 22. (a yield: 93%)

MS (MALDI-TOF-MS, m/z) 920.76 (M+)

Manufacture of Organic Thin Film Transistor

A silicon wafer substrate coated with the cleaned SiO$_2$ to be 3000 Å thick is exposed to O$_2$ plasma and then, dipped in an octadecyl trichlorosilane solution diluted in hexane to a concentration of 5 mM to change the surface to be hydrophobic. Subsequently, the fused heteroaromatic compound according to Synthesis Example 1 is vacuum-vapor deposited to be 700 Å thick by heating the substrate from room temperature to 200° C. Then, source and drain electrodes are formed thereon by using a shadow mask and depositing Au to be 1000 Å thick to manufacture an organic thin film transistor.

Charge mobility of the organic thin film transistor is calculated.

The charge mobility of the organic thin film transistor is obtained by obtaining a graph having $(I_{SD})^{1/2}$ and $V_G$ as variables from a saturation region current equation and a slope in the graph.

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

In the equations, Iso is a source-drain current, μ or μFET is charge mobility, C$_0$ is electrostatic capacity of a gate insulating layer, W is a channel width, L is a channel length, $V_G$ is a gate voltage, and $V_T$ is a threshold voltage.

A cut-off leakage current ($I_{off}$) is obtained as a minimum current in an off-state as a current flowing in an off-state. A current on-off ratio ($I_{on}/I_{off}$) is obtained as a ratio of a maximum current in an on-state relative to a minimum current in the off-state.

The charge mobility of the organic thin film transistor exhibits good charge mobility of about 2 cm$^2$/Vs.

While some example embodiments have been described, inventive concepts are not limited to the disclosed embodiments, but, on the contrary, are intended to cover various modifications and equivalent arrangements included within the spirit and scope of the appended claims.

What is claimed is:

1. A method of making a chemical product, the method comprising:

forming a first intermediate corresponding to Chemical Formula 2, the forming the first intermediate including reacting a compound corresponding to Chemical Formula 1 with a metal alkyl chalcogenide using a palladium catalyst and a tertiary phosphine catalyst,

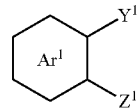

[Chemical Formula 1]

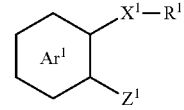

[Chemical Formula 2]

wherein, in Chemical Formulae 1 and 2,

Ar$^1$ is one of a substituted or unsubstituted aromatic ring, a substituted or unsubstituted heteroaromatic ring, and a combination thereof in a fused ring, Y$^1$ is one of a halogen element or a C1 to C10 haloalkyl group, Z$^1$ is one of a C1 to C10 alkoxy group, a C1 to C10 haloalkyl group, or a halogen element, provided that Z$^1$ is different from Y$^1$, X$^1$ is one of Se or Te, and R$^1$ is one of a substituted or unsubstituted C1 to C10 alkyl group.

2. The method of claim 1, further comprising:

forming a second intermediate corresponding to Chemical Formula 3 from the first intermediate, forming a third intermediate from the second intermediate and a compound corresponding to Chemical Formula 4:

forming a fourth intermediate including a chalcogen-containing ring from the third intermediate; and performing a cyclization reaction of the fourth intermediate to form a fused heteroaromatic compound,

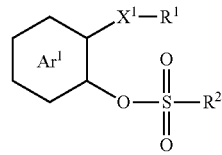

[Chemical Formula 3]

-continued

[Chemical Formula 4]

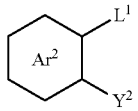

wherein, in Chemical Formulae 3 to 4, $Ar^1$ and $Ar^2$ are independently one of a substituted or unsubstituted aromatic ring, a substituted or unsubstituted heteroaromatic ring, and a combination thereof included in a fused ring, $Y^1$ and $Y^2$ are independently one of a halogen element, or a C1 to C10 haloalkyl group, $Z^1$ is one of a C1 to C10 alkoxy group, a C1 to C10 haloalkyl group, or a halogen element, provided that $Z^1$ is different from $Y^1$, $X^1$ is one of Se or Te, $R^1$ is one of a substituted or unsubstituted C1 to C10 alkyl group, $R^2$ is one of hydrogen, a substituted or unsubstituted C1 to C20 alkyl group, a C1 to C20 haloalkyl group, a substituted or unsubstituted C6 to C20 aryl group, halogen element, or a combination thereof, and $L^1$ is one of an ethenyl group or an ethynyl group.

3. The method of claim 2, wherein the tertiary phosphine catalyst includes a metal-free tertiary phosphine catalyst.

4. The method of claim 3, wherein the metal-free tertiary phosphine catalyst corresponds to Chemical Formula 5:

[Chemical Formula 5]

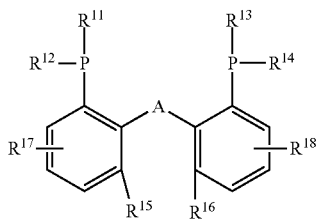

wherein, in Chemical Formula 5,

A is one of a single bond, a C1 to C3 alkylene group, or oxygen (O), $R^{11}$ to $R^{14}$ are independently one of a substituted or unsubstituted C6 to C12 aryl group, or a substituted or unsubstituted C3 to C12 cycloalkyl group, and $R^{15}$ to $R^{18}$ are independently one of hydrogen, a substituted or unsubstituted C1 to C10 alkyl group, a substituted or unsubstituted C6 to C20 aryl group, or a substituted or unsubstituted C3 to C20 cycloalkyl group, and $R^{15}$ and $R^{16}$ are independently present or are linked to provide a ring.

5. The method of claim 4, wherein the metal-free tertiary phosphine catalyst includes one of bis[2-(diphenylphosphino)phenyl]methane, bis[2-(diphenylphosphino)phenyl]ether, bis[2-(di-o-tolyphosphino)phenyl]ether, bis[2-(dicyclohexylphosphino)phenyl]ether, 4,6-bis(diphenylphosphino)dibenzofuran, or a combination thereof.

6. The method of claim 2, wherein the palladium catalyst includes tris(dibenzylideneacetone)dipalladium(0).

7. The method of claim 2, wherein the reacting the compound corresponding to Chemical Formula 1 with the metal alkyl chalcogenide includes obtaining forming the metal alkyl chalcogenide from an alkyl chalcogenide derivative and a metal salt.

8. The method of claim 7, wherein the metal salt includes at least one of an alkali metal, an alkaline-earth metal, and a transition metal.

9. The method of claim 7, wherein the metal salt includes at least one of $NaBH_4$ and $LiAlH_4$.

10. The method of claim 2, wherein the reacting the compound corresponding to Chemical Formula 1 with the metal alkyl chalcogenide includes forming the metal alkyl chalcogenide from a metal salt and a chalcogen element, and the chalcogen element is one of Se and Te.

11. The method of claim 10, wherein the metal salt includes at least one of an alkali metal, an alkaline-earth metal, and a transition metal.

12. The method of claim 10, wherein the metal salt includes at least one of methyl lithium ($LiCH_3$) and methyl magnesium bromide ($CH_3MgBr$).

13. The method of claim 2, wherein the forming the third intermediate includes supplying a halogen salt to the second intermediate.

14. The method of claim 13, wherein the forming the third intermediate includes supplying to the second intermediate one of potassium iodide, copper iodide, or a combination thereof.

15. The method of claim 2, wherein the forming the fourth intermediate includes supplying a halogen molecule to the third intermediate.

16. The method of claim 2, wherein the performing the cyclization reaction include supplying a chalcogen element to the third intermediate.

17. The method of claim 2, wherein the third intermediate corresponds to Chemical Formula 6:

[Chemical Formula 6]

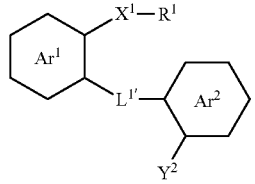

wherein, in Chemical Formula 6, $Ar^1$ and $Ar^2$ are independently one of a substituted or unsubstituted aromatic ring, a substituted or unsubstituted heteroaromatic ring, and a combination thereof in a fused ring, $X^1$ is one of Se or Te, $R^1$ is a substituted or unsubstituted C1 to C10 alkyl group, $L^{1'}$ is one of an ethenylene group or an ethynylene group, and $Y^2$ is one of a halogen element or a C1 to C10 haloalkyl group.

18. The method of claim 2, wherein the fourth intermediate corresponds to Chemical Formula 7:

[Chemical Formula 7]

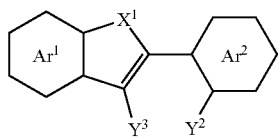

wherein, in Chemical Formula 7,
Ar¹ and Ar² are independently one of a substituted or unsubstituted aromatic ring, a substituted or unsubstituted heteroaromatic ring, and a combination thereof in a fused ring,
$X^1$ is one of Se or Te, and
$Y^2$ and $Y^3$ are independently one of a halogen element or a C1 to C10 haloalkyl group.

19. The method of claim 2, wherein the fused heteroaromatic compound corresponding to Chemical Formula 8:

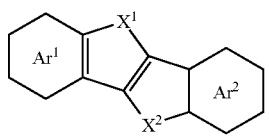

[Chemical Formula 8]

wherein, in Chemical Formula 8,
Ar¹ and Ar² are independently one of a substituted or unsubstituted aromatic ring, a substituted or unsubstituted heteroaromatic ring, and a combination thereof in a fused ring,
$X^1$ is one of Se or Te, and
$X^2$ is one of O, S, Sc, or Te.

20. The method of claim 2, wherein Ar¹ and Ar² are independently one of a benzene, a naphthalene, an anthracene, a tetracene, a pentacene, a thiophene, a selenophene, a tellurophene, a furane, a pyrrole, and a combination thereof in a fused ring.

21. The method of claim 1, wherein the tertiary phosphine catalyst includes a metal-free tertiary phosphine catalyst.

22. The method of claim 21, wherein the metal-free tertiary phosphine catalyst corresponds to Chemical Formula 5:

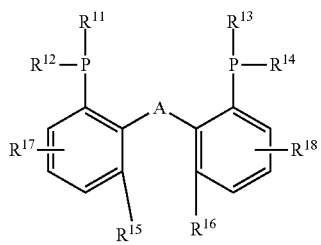

[Chemical Formula 5]

wherein, in Chemical Formula 5,
A is one of a single bond, a C1 to C3 alkylene group, or oxygen (O),
$R^{11}$ to $R^{14}$ are independently one of a substituted or unsubstituted C6 to C12 aryl group or a substituted or unsubstituted C3 to C12 cycloalkyl group, and
$R^{15}$ to $R^{18}$ are independently one of hydrogen, a substituted or unsubstituted C1 to C10 alkyl group, a substituted or unsubstituted C6 to C20 aryl group, or a substituted or unsubstituted C3 to C20 cycloalkyl group, and $R^{15}$ and $R^{16}$ are independently present or are linked to provide a ring.

23. The method of claim 22, wherein the metal-free tertiary phosphine catalyst includes one of bis[2-(diphenylphosphino)phenyl]methane, bis[2-(diphenylphosphino)phenyl]ether, bis[2-(di-o-tolyphosphino)phenyl]ether, bis[2-(dicyclohexylphosphino)phenyl]ether, 4,6-bis(diphenylphosphino)dibenzofuran, or a combination thereof.

24. The method of claim 1, wherein the palladium catalyst includes tris(dibenzylideneacetone)dipalladium(0).

25. The method of claim 1, wherein the reacting the compound corresponding to Chemical Formula 1 with the metal alkyl chalcogenide includes forming the metal alkyl chalcogenide from an alkyl chalcogenide derivative and a metal salt.

26. The method of claim 25, wherein the metal salt includes at least one of an alkali metal, an alkaline-earth metal, and a transition metal.

27. The method of claim 1, wherein
the reacting the compound represented by Chemical Formula 1 with the metal alkyl chalcogenide includes forming the metal alkyl chalcogenide from a metal salt and a chalcogen element, and
the chalcogen element is one of Se and Te.

28. The method of claim 27, wherein the metal salt includes at least one of an alkali metal, an alkaline-earth metal, and a transition metal.

29. The method of claim 1, wherein
the first intermediate is represented by Chemical Formula 2A,
the second intermediate is represented by Chemical Formula 1A,

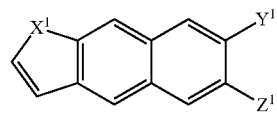

[Chemical Formula 1A]

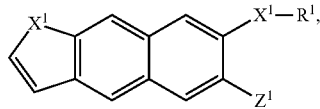

[Chemical Formula 2A]

wherein in Chemical Formulas 1A and 2A,
$Y^1$ a halogen element,
$Z^1$ is a C1 to C10 alkoxy group,
$X^1$ is one of Se or Te, and
$R^1$ is a substituted C1 to C10 alkyl group or unsubstituted C1 to C10 alkyl group.

30. The method of claim 1, wherein
Ar¹ is a fused ring that includes a substituted or unsubstituted aromatic ring and an unsubstituted heteromatic ring,
the substituted or unsubstituted aromatic ring in Ar¹ is selected from the group consisting of benzene, naphthalene, anthracene, tetracene, and pentacene,
the unsubstituted heteromatic ring in Ar¹ is selected from the group consisting of thiophene, selenophene, tellurophene, furane, and pyrrole,
$Y^1$ a halogen element,
$Z^1$ is a C1 to C10 alkoxy group,
$X^1$ is one of Se or Te, and
$R^1$ is a substituted C1 to C10 alkyl group or unsubstituted C1 to C10 alkyl group.

* * * * *